(12) United States Patent
Capala et al.

(10) Patent No.: US 8,303,960 B2
(45) Date of Patent: Nov. 6, 2012

(54) RADIOLABELED AFFIBODY MOLECULES

(75) Inventors: Jacek Capala, Gaithersburg, MD (US); Dale O. Kiesewetter, Gaithersburg, MD (US); Gabriela Kramer-Marek, Washington, DC (US); Sang Bong Lee, Rockville, MD (US)

(73) Assignee: The United States of America, as represented by the Secretary, Department of Health and Human ServicesDC (US)

( * ) Notice: Subject to any disclaimer, the term of this patent is extended or adjusted under 35 U.S.C. 154(b) by 91 days.

(21) Appl. No.: 12/528,823

(22) PCT Filed: Feb. 27, 2008

(86) PCT No.: PCT/US2008/055144
§ 371 (c)(1),
(2), (4) Date: May 17, 2010

(87) PCT Pub. No.: WO2008/118601
PCT Pub. Date: Oct. 2, 2008

(65) Prior Publication Data
US 2010/0254899 A1 Oct. 7, 2010

Related U.S. Application Data
(60) Provisional application No. 60/891,875, filed on Feb. 27, 2007.

(51) Int. Cl.
*A61K 51/08* (2006.01)
*A61K 51/00* (2006.01)
*A61K 38/16* (2006.01)
*C07K 16/00* (2006.01)

(52) U.S. Cl. .................. 424/193.1; 424/1.49; 424/1.53; 424/1.89; 424/9.1; 424/9.3; 424/1.57; 530/391.3

(58) Field of Classification Search .......................... None
See application file for complete search history.

(56) References Cited

U.S. PATENT DOCUMENTS

| 4,261,989 | A | 4/1981 | Sasaki et al. |
| 5,831,012 | A | 11/1998 | Nilsson et al. |
| 6,747,055 | B1 | 6/2004 | Ho et al. |
| 6,890,917 | B2 | 5/2005 | Snader et al. |
| 7,026,350 | B2 | 4/2006 | Ho et al. |
| 7,902,332 | B2 * | 3/2011 | De Jesus et al. .............. 530/345 |
| 2008/0139787 | A1 | 6/2008 | De Jesus et al. |

OTHER PUBLICATIONS

Cai et al., *J. Nucl. Med.*, 47(7), 1172-1180 (2006).
Kiesewetter et al., *Nuclear Medicine and Biology*, 30, 11-24 (2003).
Kramer-Marek et al., *Eur. J. Nuclear Med. Mol. Imaging*, 35, 1008-1009 (2008).
Mass., *Int. J. Radiation Oncology Biol. Phys.*, 58 (3), 932-940 (2004).
Mume et al., *Biconjugate Chem.*, 16, 1547-1555 (2005).
Mume et al., *Nuclear Medicine Biology*, 32 (6), 613-622 (2005).
Nicholson et al., *Eur. J. Cancer*, 37 (Suppl. 4), S9-S15 (2001).
Nilsson et al, *Protein Engineering*, 1 (2), 107-113 (1987).
Orlova et al., *Cancer Res.*, 66 (8), 4339-4348 (2006).
Orlova et al., *J. Nucl. Med.*, 47 (3), 512-519 (2006).
Scholl et al., *Annals of Oncology*, 12 (Suppl 1), S81-S87 (2001).
Seidel et al., *IEEE Transactions on Nuclear Science*, 50 (5), 1347-1350 (2003).
Steffen et al., *Cancer Biotheraphy Radiopharm.*, 20 (3), 239-248 (2005).
Tran et al., *Int. J. Mol Med.*, 19 (3), 485-493 (2007).
Uhlen et al, *J. Bio. Chem.*, 259 (3), 1695-1702 (1984).
Wang et al., *Semin. Oncol.*, 28 (5 Suppl. 16), 115-124 (2001).
Wikman et al., *Protein Eng. Design and Selection*, 17 (5), 455-462(2004).
Altai et al., "Order of amino acids in C-terminal cysteine-containing peptide-based chelators influences cellular processing and biodistribution of (99m)Tc-labeled recombinant Affibody molecules," *Amino Acids*, 42 (5), 1975-1985 (2012).
Altai et al., "Preclinical evaluation of anti-HER2 Affibody molecules site-specifically labeled with (111)In using a maleimido derivative of NODAGA," *Nucl. Med. Biol.*, 39 (4), 518-529 (2012).
Andersen et al., "Extending half-life by indirect targeting of the neonatal Fc receptor (FcRn) using a minimal albumin binding domain," *J. Biol. Chem.*, 286 (7), 5234-5241 (2011).
Barta et al., "Protein interactions with HER-family receptors can have different characteristics depending on the hosting cell line," *Int. J. Oncol.*, 40 (5), 1677-1682 (2012).
Baum et al., "Molecular Imaging of HER2-Expressing Malignant Tumors in Breast Cancer Patients Using Synthetic 111In- or 68Ga-Labeled Affibody Molecules," *J. Nucl. Med.*, 51, 892-897 (2010).
Cao et al., "Phage-based molecular directed evolution yields multiple tandem human IgA affibodies with intramolecular binding avidity," *J. Biotechnol.*, 158 (3), 120-127 (2012).
Capala et al., "Molecular imaging of HER2-positive breast cancer: a step toward an individualized 'image and treat' strategy," *Curr. Opin. Oncol.*, 22 (6), 559-566 (2010).
Chang et al., "Engineering of *Escherichia coli* for targeted delivery of transgenes to HER2/neu-positive tumor cells," *Biotechnol. Bioeng.*, 108 (7), 1662-1972 (2011).
Chiang et al., "Caleosin-assembled oil bodies as a potential delivery nanocarrier," *Appln. Microbiol. Biotechnol.*, 93 (5), 1905-1915 (2012).
Chiang et al., "Functionalized nanoscale oil bodies for targeted delivery of a hydrophobic drug" *Nanotechnology*, 22 (1), 1-9 (2011).
Chiang et al., "Selective internalization of self-assembled artificial oil bodies by HER2/neu-positive cells," *Nanotechnology*, 22 (1), 1-11 (2011).
Chopra, "[99mTc(CO)3]+-Labeled anti-epidermal growth factor receptor (HER2) affibody ZHER2:342 with a hexa-histidine tag (H6) on the C-terminal," *National Center for Biotechnology Information*, 1-5 (2011).

(Continued)

*Primary Examiner* — Phuong Huynh
(74) *Attorney, Agent, or Firm* — Leydig, Voit & Mayer

(57) ABSTRACT

The invention provides a radiolabeled affibody molecule comprising a fragment of an IgG-binding domain of protein A from *Staphylococcus aureus*, a bifunctional linker, and a radiolabel comprising $^{18}$F or $^{76}$Br, wherein the bifunctional linker links the fragment and the radiolabel. The affibody molecule binds with high affinity to select receptors, which are over-expressed in certain cancers. Since the radionuclides emit a positron, the in vitro and in vivo binding characteristics of the radiolabeled affibody can be assessed using diagnostic imaging.

17 Claims, 10 Drawing Sheets

OTHER PUBLICATIONS

Chopra, "[99mTc(CO)3]+-Labeled anti-epidermal growth factor receptor (HER2) affibody ZHER2:342 with a hexa-histidine tag (H6) on the N-terminal," *National Center for Biotechnology Information*, 1-5 (2011).

Chopra, "[99mTc(CO)3]+-Labeled anti-epidermal growth factor receptor (HER2) affibody ZHER2:342 with a tri-(histidine-glutamate) peptide tag (HE)3 on the N-terminal," *National Center for Biotechnology Information*, 1-6 (2011).

Chopra, "111In-Labeled affibody ABY-025 targeting epidermal growth factor receptor 2," *National Center for Biotechnology Information*, 1-5 (2010).

Chopra, "111In-Labeled DOTA-conjugated 6-aminohexanoic linker-containing variant of anti-epidermal growth factor receptor 2 Affibody ZHER2:342 (ABY-003)," *National Center for Biotechnology Information*, 1-5 (2011).

Chopra, "111In-Labeled human serum albumin-conjugated Affibody Z HER2:342 that targets the human epidermal growth factor receptor 2 (HER2)," *National Center for Biotechnology Information*, 1-4 (2011).

Chopra, "64Cu-Labeled human serum albumin-conjugated Affibody Z HER2:342 that targets the human epidermal growth factor receptor 2 (HER2)," *National Center for Biotechnology Information*, 1-4 (2011).

De Vrij et al., "A cathepsin-cleavage site between the adenovirus capsid protein IX and a tumor-targeting ligand improves targeted transduction," *Gene Ther.*, 1-8 (2011).

Eigenbrot et al., "Structural basis for high-affinity HER2 receptor binding by an engineered protein," *Proc. Natl. Acad. Sci.*, 107 (34), 15039-15044 (2010).

Gao et al., "Affibody-based nanoprobes for HER2-expressing cell and tumor imaging," *Biomaterials*, 32 (8), 2141-2148 (2011).

Gopal et al., "Structure prediction and validation of an affibody engineered for cell-specific nucleic acid targeting," *Syst. Synth. Biol.*, 4 (4), 293-297 (2010).

Govindarajan et al., "Targeting human epidermal growth factor receptor 2 by a cell-penetrating peptide-affibody bioconjugate," *Biomaterials*, 33 (8), 2570-2582 (2012).

Grimm et al., "Ribosome display selection of a murine IgG$_1$ Fab binding affibody molecule allowing species selective recovery of monoclonal antibodies," *Mol. Biotechnol.*, 48 (3), 263-276 (2011).

Grimm et al., "Selection and characterisation of affibody molecules inhibiting the interaction between Ras and Raf in vitro," *N. Biotechnol.*, 27 (6), 766-773 (2010).

Haggblad et al., "The effect of a dimeric Affibody molecule (ZEGFR:1907)2 targeting EGFR in combination with radiation in colon cancer cell lines," *Int. J. Oncol.*, 40 (1), 176-184 (2012).

Hassan et al., "In Vivo Method to Monitor Changes in HER2 Expression Using Near-Infrared Fluorescence Imaging," *Mol. Imaging*, 1-10 (2011).

Heskamp et al., "Imaging of human epidermal growth factor receptor type 2 expression with 18F-labeled affibody molecule ZHER2:2395 in a mouse model for ovarian cancer," *J. Nucl. Med.*, 53 (1), 146-153 (2012).

Hofstrom et al., "Use of a HEHEHE purification tag instead of a hexahistidine tag improves biodistribution of affibody molecules site-specifically labeled with (99m)Tc, (111)In, and (125)I," *J. Med. Chem.*, 54 (11), 3817-3826 (2011).

Hoppmann et al., "Radiolabeled affibody-albumin bioconjugates for HER2-positive cancer targeting," *Bioconjug. Chem.*, 22 (3), 413-421 (2011).

Jokerst et al., "Affibody-functionalized gold-silica nanoparticles for Raman molecular imaging of the epidermal growth factor receptor," *Small*, 7 (5), 625-633 (2011).

Kramer-Marek et al., "68Ga-DOTA-affibody molecule for in vivo assessment of HER2/neu expression with PET," *Eur. J. Nucl. Med. Mol. Imaging*, 38 (11), 1967-1976 (2011).

Kramer-Marek et al., "Changes in HER2 Expression in Breast Cancer Xenografts After Therapy Can Be Quantified Using PET and 18F-Labeled Affibody Molecules," *J. Nucl. Med.*, 50, 1131-1139 (2009).

Kronqvist et al., "Combining phage and staphylococcal surface display for generation of ErbB3-specific Affibody molecules," *Protein Eng. Des. Sel.*, 24 (4), 385-396 (2011).

Lang et al., "New Methods for Labeling RGD Peptides with Bromine-76," *Theranostics*, 1, 341-353 (2011).

Laverman et al., "Optimized labeling of NOTA-conjugated octreotide with F-18," *Tumour Biol.*, 33 (2), 427-434 (2012) (Published Online 2011).

Leung, "111In-1,4,7,10-tetraazacyclododecane-1,4,7-tris-acetic acid-10-maleimidoethylacetamide-Affibody ZHER2:2395-Cys," *National Center for Biotechnology Information*, 1-4 (2009).

Leung, "68Ga-1,4,7,10-Tetraazacyclododecane-N,N',N'',N'''-tetraacetic acid-synthetic HER2 specific Affibody ZHER2:342-pep2," *National Center for Biotechnology Information*, 1-4 (2010).

Leung, "68Ga-Labeled anti-EpCAM diabody against epithelial cell adhesion molecule," *National Center for Biotechnology Information*, 1-3 (2010).

Leung, "99mTc-Mercaptoacetyl-Glu-Glu-Glu-Affibody ZHER2:342," *National Center for Biotechnology Information*, 1-4 (2008).

Leung, "99mTc-Mercaptoacetyl-Gly-Gly-Gly-Affibody ZHER2:342," *National Center for Biotechnology Information*, 1-4 (2008).

Leung, "99mTc-Mercaptoacetyl-Ser-Ser-Ser-Affibody ZHER2:342," *National Center for Biotechnology Information*, 1-4 (2008).

Leung, "Alexa Fluor 750-albumin-binding domain-fused-(ZHER2:342)2 Affibody," *National Center for Biotechnology Information*, 1-4 (2011).

Leung, "Alexa Fluor 750-ZHER2:342 Affibody," *National Center for Biotechnology Information*, 1-4 (2011).

Leung, "DY-682—Labeled albumin-binding domain—fused-ZHER2:342 Affibody," *National Center for Biotechnology*, 1-4 (2010).

Leung, "IRDye 800-Labeled anti—epidermal growth factor receptor Affibody," *National Center for Biotechnology*, 1-4 (2011).

Li et al., "Conjugated polymer loaded nanospheres with surface functionalization for simultaneous discrimination of different live cancer cells under single wavelength excitation," *Anal. Chem.*, 83 (6), 2125-2132 (2011).

Lindberg et al., "Evaluation of a HER2-targeting affibody molecule combining an N-terminal HEHEHE-tag with a GGGC chelator for (99m)Tc-labelling at the C terminus," *Tumour Biol.*, 33 (3), 641-651 (2012).

Lindborg et al., "Engineered high-affinity affibody molecules targeting platelet-derived growth factor receptor β in vivo," *J. Mol. Biol.*, 407 (2), 298-315 (2011).

Lindgren et al., "N-terminal engineering of amyloid-β-binding Affibody molecules yields improved chemical synthesis and higher binding affinity," *Protein Sci.*, 19 (12), 2319-2329 (2010).

Magnusson et al., "A transductionally retargeted adenoviral vector for virotherapy of Her2/neu-expressing prostate cancer," *Hum. Gene Ther.*, 23 (1), 70-82 (2012).

Malmberg et al., "Comparative biodistribution of imaging agents for in vivo molecular profiling of disseminated prostate cancer in mice bearing prostate cancer xenografts: focus on 111In- and 125I-labeled anti-HER2 humanized monoclonal trastuzumab and ABY-025 affibody," *Nucl. Med. Biol.*, 38 (8), 1093-1102 (2011).

Malmberg et al., "Comparative evaluation of synthetic anti-HER2 Affibody molecules site-specifically labelled with 111In using N-terminal DOTA, NOTA and NODAGA chelators in mice bearing prostate cancer xenografts," *Eur. J. Nucl. Med. Mol. Imaging*, 39, 481-492 (2012).

Malmberg et al., "Imaging agents for in vivo molecular profiling of disseminated prostate cancer—targeting EGFR receptors in prostate cancer: comparison of cellular processing of [111In]-labeled affibody molecule Z(EGFR:2377) and cetuximab," *Int. J. Oncol.*, 38 (4), 1137-1143 (2011).

Miao et al., "A novel 18F-labeled two-helix scaffold protein for PET imaging of HER2-positive tumor," *Eur. J. Nucl. Med. Imaging*, 38 (11), 1977-1984 (2011).

Pu et al., "Affibody-attached hyperbranched conjugated polyelectrolyte for targeted fluorescence imaging of HER2-positive cancer cell," *Biomacromolecules*, 12 (8), 2966-2974 (2011).

Qiao et al., "HER2 targeted molecular MR imaging using a de novo designed protein contrast agent" *PLos One*, 6 (3), 1-9 (2011).

Qvarnstrom et al., "Effects of affinity on binding of HER2-targeting Affibody molecules: model experiments in breast cancer spheroids," *Int. J. Oncol.*, 39 (2), 353-359 (2011).

Ravnikar et al., "Engineered lactic acid bacterium Lactococcus lactis capable of binding antibodies and tumor necrosis factor alpha," *Appl. Environ. Microbio.*, 76 (20), 6928-6932 (2010).

Reilly, "Aiming for a Direct Hit: Combining Molecular Imaging with Targeted Cancer Therapy," *J. Nucl. Med.*, 50 (7), 1017-1019 (2009).

Ren et al., "In vivo targeting of HER2-positive tumor using 2-helix affibody molecules," *Amino Acids.*, (2011).

Rosik et al., "Direct comparison of 111In-labelled two-helix and three-helix Affibody molecules for in vivo molecular imaging," *Eur. J. Nucl. Med. Mol. Imaging*, 39 (4), 693-702 (2012).

Sandstrom et al., "Improved tumor-to-organ ratios of a novel 67Ga-human epidermal growth factor radionuclide conjugate with preadministered antiepidermal growth factor receptor affibody molecules," *Cancer Biother. Radiopharm.*, 26 (5) 593-601 (2011).

Shan, "111In-Labeled 1,4,7,10-tetraazacyclododecane-1,4,7,10-tetraacetic acid-VENK[homoC]NKEMRNRYWEAALDPNLN-NQQKRAKIRSIYDDP[homoC]-NH2 with a disulfide bridge between the two homoC," *National Center for Biotechnology Information*, 1-4 (2011).

Shan, "18F-Labeled N-(4-fluorobenzylidene)oxime-dimeric (ZHER2:477)2," *National Center for Biotechnology Information*, 1-5 (2012).

Shan, "18F-Labeled N-(4-fluorobenzylidene)oxime-monomeric ZHER2:477," *National Center for Biotechnology Information*, 1-5 (2012).

Shan, "18F-Labeled N-(4-fluorobenzylidene)oxime-VENK[homoC]NKEMRNRYWEAALDPNLN-NQQKRAKIRSIYDDP[homoC]-NH2 with a disulfide bridge between the two homoC," *National Center for Biotechnology Information*, 1-4 (2012).

Shan, "64Cu-1,4,7,10-Tetraazacyclododecane-1,4,7-β max tris(acetic acid)-10-acetate mono(N-ethylmaleimide amide)-dimeric (ZHER2:477)2 ," *National Center for Biotechnology Information*, 1-5 (2011).

Shan, "64Cu-1,4,7,10-Tetraazacyclododecane-1,4,7-β max tris(acetic acid)-10-acetate mono(N-ethylmaleimide amide)-monomeric ZHER2:477," *National Center for Biotechnology Information*, 1-5 (2011).

Shan, "64Cu-Labeled 1,4,7,10-tetraazacyclododecane-1,4,7,10-tetraacetic acid-VENK[homoC]NKEMRNRYWEAALDPNLN-NQQKRAKIRSIYDDP[homoC]-NH2 with a disulfide bridge between the two homoC," *National Center for Biotechnology Information*, 1-4 (2011).

Shan, "68Ga-Labeled 1,4,7,10-tetraazacyclododecane-1,4,7,10-tetraacetic acid-VENK[homoC]NKEMRNRYWEAALDPNLN-NQQKRAKIRSIYDDP[homoC]-NH2 with a disulfide bridge between the two homoC," *National Center for Biotechnology Information*, 1-4 (2012).

Shishido et al., "Affibody-displaying bionanocapsules for specific drug delivery to HER2-expressing cancer cells," *Bioorg. Med. Chem. Lett.*, 20 (19), 5726-5731 (2010).

Smith et al., "Hyperthermia-triggered intracellular delivery of anti-cancer agent to HER2(+) cells by HER2-specific affibody (ZHER2-GS-Cys)-conjugated thermosensitive liposomes (HER2(+) affisomes)," *J. Control Release*, 153 (2),187-194 (2011).

Thakor et al., "The fate and toxicity of Raman-active silica-gold nanoparticles in mice," *Sci. Transl. Med.*, 3 (79), 79ra33, 1-11 (2011).

Tolmachev et al., "Evaluation of a maleimido derivative of NOTA for site-specific labeling of affibody molecules," *Bioconjug. Chem.*, 22 (5), 894-902 (2011).

Tolmachev et al., "HEHEHE-tagged affibody molecule may be purified by IMAC, is conveniently labeled with [$^{99}$(m)Tc(CO)$_3$](+), and shows improved biodistribution with reduced hepatic radioactivity accumulation," *Bioconjug. Chem.*, 21 (11), 2013-2022 (2010).

Tolmachev et al., "Imaging of insulinlike growth factor type 1 receptor in prostate cancer xenografts using the affibody molecule 111In-DOTA-ZIGF1R:4551," *J. Nucl. Med.*, 53 (1), 90-97 (2012).

Tolmachev et al., "Influence of an aliphatic linker between DOTA and synthetic Z(HER2:342) Affibody molecule on targeting properties of the (111)In-labeled conjugate," *Nucl. Med. Biol.*, 38 (5), 697-706 (2011).

Tolmachev et al., "Optimal specific radioactivity of anti-HER2 Affibody molecules enables discrimination between xenografts with high and low HER2 expression levels," *Eur. J. Nucl. Med. Mol. Imaging*, 38 (3), 531-539 (2011).

Van De Ven et al., "Optical imaging with her2-targeted affibody molecules can monitor hsp90 treatment response in a breast cancer xenograft mouse model," *Clin. Cancer Res.*, 18 (4), 1073-1081 (2012).

Wallberg et al., "Affinity recovery of eight HER2-binding affibody variants using an anti-idiotypic affibody molecule as capture ligand," *Protein Expr. Purif.*, 76 (1), 127-135 (2011).

Wallberg et al., "Molecular design and optimization of 99mTc-labeled recombinant affibody molecules improves their biodistribution and imaging properties," *J. Nucl. Med.*, 52 (3), 461-469 (2011).

Zielinski et al., "HER2-affitoxin: a potent therapeutic agent for the treatment of HER2-overexpressing tumors," *Clin. Cancer Res.*, 17 (15), 5071-5081 (2011).

Grimm et al., "Monitored whole gene in vitro evolution of an anti-hRaf-1 affibody molecule towards increased binding affinity,"*N. Biotechnol.* 29 (5), 534-542 (2011).

* cited by examiner

FIGURE 4A
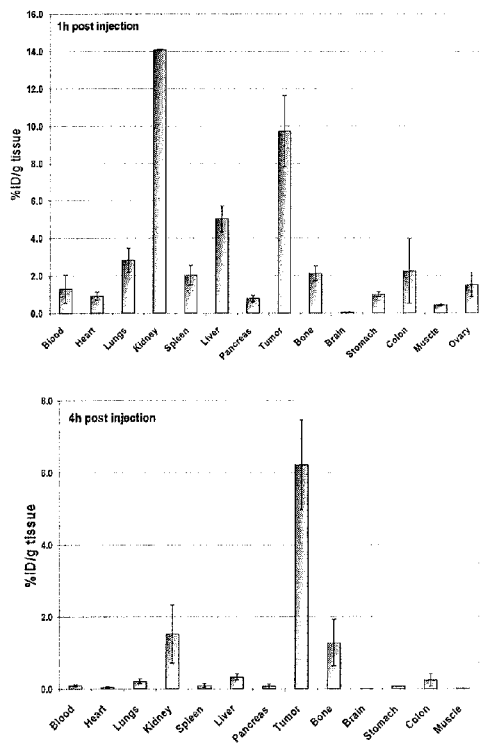
FIGURE 4B
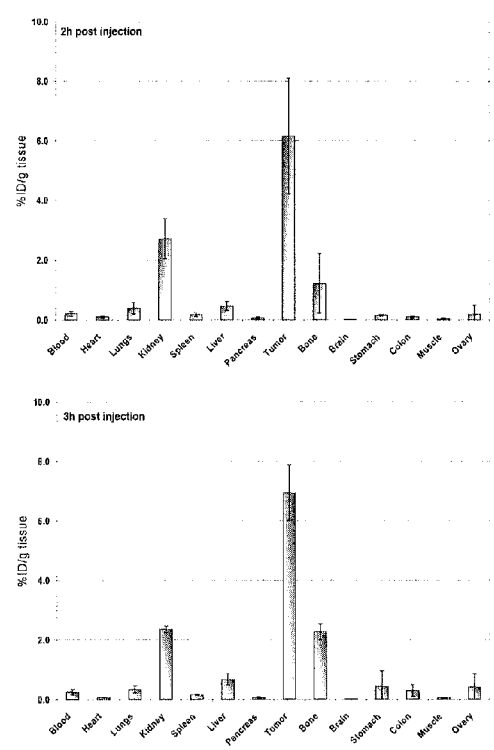
FIGURE 4C
FIGURE 4D

SEQUENCE LISTING

```
<160> NUMBER OF SEQ ID NOS: 1

<210> SEQ ID NO 1
<211> LENGTH: 58
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (9)..(11)
<223> OTHER INFORMATION: "Xaa" is any amino acid.
<220> FEATURE:
<221> NAME/KEY: MISC_FEATURE
<222> LOCATION: (13)..(14)
<223> OTHER INFORMATION: "Xaa" is any amino acid.
<220> FEATURE:
<221> NAME/KEY: MISC_FEATURE
<222> LOCATION: (17)..(18)
<223> OTHER INFORMATION: "Xaa" is any amino acid.
<220> FEATURE:
<221> NAME/KEY: MISC_FEATURE
<222> LOCATION: (24)..(25)
<223> OTHER INFORMATION: "Xaa" is any amino acid.
<220> FEATURE:
<221> NAME/KEY: MISC_FEATURE
<222> LOCATION: (27)..(28)
<223> OTHER INFORMATION: "Xaa" is any amino acid.
<220> FEATURE:
<221> NAME/KEY: MISC_FEATURE
<222> LOCATION: (32)..(32)
<223> OTHER INFORMATION: "Xaa" is any amino acid.
<220> FEATURE:
<221> NAME/KEY: MISC_FEATURE
<222> LOCATION: (35)..(35)
<223> OTHER INFORMATION: "Xaa" is any amino acid.

<400> SEQUENCE: 1

Val Asp Asn Lys Phe Asn Lys Glu Xaa Xaa Xaa Ala Xaa Xaa Glu Ile
1               5                   10                  15

Xaa Xaa Leu Pro Asn Leu Asn Xaa Xaa Gln Xaa Xaa Ala Phe Ile Xaa
            20                  25                  30

Ser Leu Xaa Asp Asp Pro Ser Gln Ser Ala Asn Leu Leu Ala Glu Ala
        35                  40                  45

Lys Lys Leu Asn Asp Ala Gln Ala Pro Lys
    50                  55
```

RADIOLABELED AFFIBODY MOLECULES

CROSS-REFERENCE TO RELATED APPLICATIONS

This patent application claims the benefit of U.S. Provisional Patent Application No. 60/891,875, filed Feb. 27, 2007, which is incorporated by reference.

BACKGROUND OF THE INVENTION

Imaging techniques such as magnetic resonance imaging (MRI), positron emission tomography (PET), and computed tomography (CT scan) provide non-destructive diagnostic examination of tissues or organs. In particular, PET involves the acquisition of physiologic images based on the detection of positron radiation emitted from a radioactive substance administered to the patient. The subsequent images of the human body developed with this technique are used to evaluate a variety of diseases, particularly cancer. Targeted delivery of the radioactive substance to the tissue or organ has advantages such as excellent specificity and high binding affinity, and therefore, has received considerable attention from the industry. Accordingly, there is a desire for substances that target and deliver positron-emitting radionuclides to selected organs or tissues.

BRIEF SUMMARY OF THE INVENTION

The invention provides a radiolabeled affibody molecule comprising a fragment of an IgG-binding domain of protein A from *Staphylococcus aureus*, a bifunctional linker, and a radiolabel. The bifunctional linker links the fragment and the radiolabel. The affibody molecule binds, advantageously, with high affinity to select receptors that are over-expressed in certain cancers (e.g., breast, lung, prostate, gastro-intestinal, and/or ovarian cancer). In an embodiment, since the radionuclides emit a positron, the in vitro and in vivo binding characteristics of the radiolabeled affibody can be assessed using diagnostic imaging, such as positron emission tomography (PET). Since PET is a quantitative tool, the present invention provides a method of measuring the quantity of a receptor, such as HER2 or EGFR that is overexpressed in a tissue or organ of a subject.

The present invention thus provides a molecular probe to assess global (as opposed to local biopsy) expression of growth factor receptors expression in vivo. The molecular characteristics of the affibody molecules combined with quantitative nature of PET imaging provide in vivo quantification of the growth factor receptors that is advantageous for selection of patients for molecularly targeted therapies aimed at these receptors and for monitoring the tumor response to those therapies. Accordingly, the present invention provides a method of quantifying a growth factor receptor (e.g., HER2 or EGFR) in a tissue or organ of a subject before and after administration of an agent that decreases the growth factor receptor.

BRIEF DESCRIPTION OF THE SEVERAL VIEWS OF THE DRAWINGS

FIG. 2A shows a binding saturation assay using SKBR-3 cells (concentration of radiolabeled affibody molecule versus concentration bound: NSB=non specific binding obtained by saturation of the receptors with 100-fold excess of non-labeled affibody (▼) TB=total binding (●), and SB=specific binding (○)). FIG. 2B depicts a competition binding assay using SKOV-3 cells (log of concentration of competitor compound versus percent of radiolabeled affibody molecule bound).

FIG. 4 (panels A-D) illustrates the radioactivity accumulated in various organs of athymic nude mice bearing HER2 positive SKOV-3 xenografts at different times post i.v. injection of $^{18}$F-$Z_{HER2}$-affibody molecules (~50-60 microCi) in accordance with an embodiment of the invention. FIG. 4A represents 1 h post-injection. FIG. 4B represents 2 h post-injection. FIG. 4C represents 3 h post-injection. FIG. 4D represents 4 h post-injection.

DETAILED DESCRIPTION OF THE INVENTION

Figure 1A:
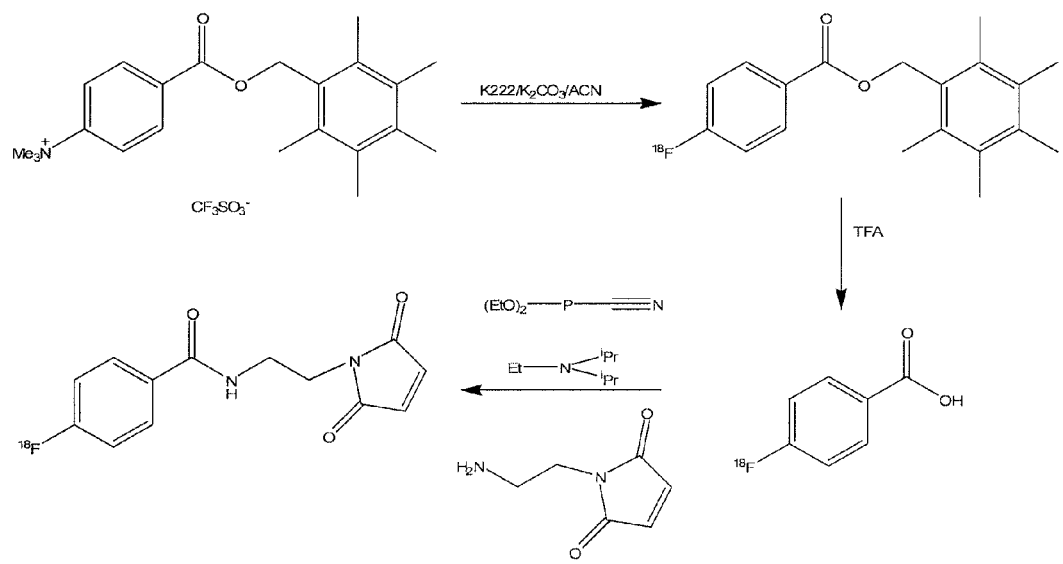
FIG. 1A depicts a preparation of N-[2-(4-[$^{18}$F]fluorobenzamide)ethyl]maleimide, an intermediate in preparing an $^{18}$F labeled affibody molecule in accordance with an embodiment of the invention.

The present invention, in accordance with an embodiment, is directed to radiolabeled affibody molecule comprising a fragment of an IgG-binding domain of protein A from *Staphylococcus aureus*, a bifunctional linker, and a radiolabel comprising $^{18}$F or $^{76}$Br, wherein the bifunctional linker links the fragment and the radiolabel.

Affibody® (hereinafter "affibody") molecules are small highly robust proteins with specific affinities to target proteins. They can be designed and used, for example, like aptamers. Affibody molecules in accordance with the invention comprise a backbone derived from an IgG-binding domain of Staphlococcal Protein A (Protein A produced by *S. aureus*). The backbone can be derived from an IgG binding domain comprising the three alpha helices of the IgG-binding domain of Staphylococcal Protein A termed the B domain. The amino acid sequence of the B domain is described in Uhlen et al., *J. Biol. Chem.* 259: 1695-1702 (1984). Alternatively, the backbone can be derived from the three alpha helices of the synthetic IgG-binding domain known in the art as the Z domain, which is described in Nilsson et al., *Protein Eng.* 1: 107-113 (1987). The backbone of an affibody comprises the amino acid sequences of the IgG binding domain with amino acid substitutions at one or more amino acid positions. The affibody, for example, comprises the 58 amino acid sequence of the Z domain (VDNKFNKEXXXAXXEIXXLPNLNXXQXXAHXSLXDDPSQSANLLAEAKKLNDAQAPK (SEQ ID NO: 1)), wherein X at each of positions 9, 10, 11, 13, 14, 17, 18, 24, 25, 27, 28, 32, and 35 is any amino acid.

Affibody molecules with specificity and selectivity for tumor markers can be used for non-invasive early detection of tumors, and to monitor disease by detecting tumor progression or regression in response to cancer therapy. The small size of the affibody molecules, compared to larger molecules, such as antibodies, gives access into solid tumors and rapid clearance from the blood stream. The affibody molecule constitutes a highly suitable carrier for directing radioisotopes and other toxins to tumor cells due to specific target binding and lack of irrelevant interactions, such as the Fc receptor binding displayed by some antibodies. High contrast tumor images can be visualized given the strong and/or specific binding of the affibody molecules in accordance with an embodiment of the invention.

Embodiments of radiolabeled affibody molecules show specific binding to HER2 receptors and is not affected by pretreatment of the target tumor cells with Herceptin™. Thus, the radiolabeled affibody molecules bind to an epitope that is not the target for Herceptin™. This advantages enables, for example, monitoring of receptor expression in patients undergoing treatment with Herceptin™ and allows not only non-invasive identification of patients suitable for targeted therapy designed against HER2-positive tumors but also provides means to monitor the immediate response (e.g., receptor down-regulation) to therapy. Further, this leads to the advantage that it is possible to adjust dosage and timing of receptor-targeted therapeutic agents' application for individual patients based on the actual status of those receptors and, if some of the metastases are shown not to respond to the therapy, alternative approaches could be applied.

With respect to the present invention, in an embodiment, the affibody which binds to HER2 or EGFR can be obtained by constructing a library of affibodies (an affibody library), wherein the library comprises a plurality of affibodies, each comprising SEQ ID NO: 1 and comprising a different amino acid sequence, wherein the variation of amino acid sequence is at one or more of positions 9, 10, 11, 13, 14, 17, 18, 24, 25, 27, 28, 32, and 35 of SEQ ID NO: 1. U.S. Pat. No. 5,831,012, which is incorporated herein by reference, describes a method of constructing such an affibody library. The affibody library can then be screened for affibodies which bind to the HER2 or EGFR protein by methods known in the art. Comparatively, antibodies are produced in mammalian cells, which is associated with a significantly higher cost due to the fermentation and purification process.

Preferably, the affibody molecule is a specific affinity ligand selected against an extra cellular domain of HER2 or EGFR (e.g., anti-HER2 Affibody and anti-EGFR Affibody, which are available from Affibody AB (Bromma, Sweden)). The Anti-HER2 Affibody molecule is modified with a C-terminal cysteine residue, thereby providing a terminal thiol group. Preferably, the affibody molecule comprises the amino acid sequence of SEQ ID NO: 1 and binds to HER2, EGFR, or both. Suitable affibody molecules with high affinity for HER2 are suitable for use in the present invention, such as $Z_{HER2:4}$, $(Z_{HER2:4})_2$-Cys, $His_6$-$(Z_{HER2:4})_2$, $Z_{HER2:342}$, $Z_{HER2:7}$, $Z_{HER2:342}$, $Z_{HER2:24}$, $Z_{HER2:79}$, $Z_{HER2:2}$, $Z_{HER2:8}$, $Z_{HER2:25}$, $Z_{HER2:mat}$, $Z_{HER2:470}$, $Z_{HER2:382}$, $Z_{HER2:477}$, $Z_{HER2:492}$, $Z_{HER2:475}$, $Z_{HER2:473}$, $Z_{HER2:489}$, $Z_{HER2:487}$, $Z_{HER2:336}$, $His_6$-$Z_{HER2:342}$, and $His_6$-$Z_{HER2:7}$ (see, e.g., Wikman et al., *Protein Engineering, Design and Selection*, 17(5): 455-462 (2004), Mume et al., *Bioconjugate Chem.*, 16: 1547-1555 (2005), Wikman, M. Ph.D. Thesis, "Rational and combinatorial protein engineering for vaccine delivery and drug targeting," 2005, School of Biotechnology, Royal Institute of Technology, Albanova University Center, Stockholm, Sweden, ISBN 91-7178-003-3, Steffen et al., *Cancer Biother. Radiopharm.*, 20: 239-248 (2005), and Orlova et al., *Cancer Research*, 66(8): 4339-4348 (April 2006)). Preferably, the affibody molecule comprises a $His_6$-$Z_{HER2:342}$ fragment of an IgG-binding domain of protein A from *Staphylococcus aureus*.

Affibody molecules comprising a terminal thiol group (e.g., that of a cysteine residue) or an alpha or epsilon amino group can be synthesized chemically or in bacteria or purchased from a commercial source (e.g., Affibody AB, Bromma, Sweden). In an embodiment, basic peptide synthesis can ensure that the affibody comprises a terminal thiol group of a cysteine residue.

Alternatively, a terminal thiol group can be incorporated artificially, for example, by way of reagents such as SATA (N-succinimidyl-S-acetylthioacetate), SATP (N-succinimidyl-S-acetylthiopropionate), or Traut's Reagent (2-iminothiolane) that convert amino groups to thiol groups. Both SATA and SATP form protected thiol groups, which can be deprotected with conventional reagents (e.g., hydroxylamine).

The bifunctional linker is covalently bonded to the radiolabel and a group on the affibody residue, such as a terminal thiol group or an alpha or epsilon amino group. Any suitable linker can be used. Examples of suitable linkers include products of cross-linking reagents that are commercially available (e.g., Pierce Chemical Co.). Typically, the cross-linking reagents contain reactive groups at their ends that are capable of linking to the thiol or amino group on the affibody fragment and the radiolabel, thereby reducing the potential for unwanted side reactions. A wide variety of cross-linking reagents are available that are capable of reacting with the thiol or amino group on the affibody fragment and the radiolabel. Preferably, the bifunctional linker is a product of a cross-linking reagent that comprises an active ester, aryl, isothiocyano, isocyano, carboxy, acyl, halo, maleimido, or active disulfido group, provided that when the radiolabel is $^{76}$Br, then the bifunctional linker does not include a phenolic OH group. Preferably, these cross-linking reagents react first with the radiolabel, and subsequently with the terminal thiol (—SH) group or alpha or epsilon amino group on the affibody fragment.

In accordance with an embodiment of the invention, the maleimide group reacts with thiol (—SH) groups at pH 6.5-7.5 to form a stable thioether bond. The terminal thiol group is attached to the desired bifunctional linker via the carbon-carbon double bond of the maleimide group, thereby forming a heterocyclic imido group. Thus, the bifunctional linker in the affibody molecule preferably comprises an imido group, particularly a heterocyclic imido group (e.g., 2,5-dioxopyrrolidin-1-yl), linking the terminal thio group of the affibody fragment. Preferably, the bifunctional linker also comprises an aryl group linking the radiolabel (e.g., at the 2-, 3-, or 4-position), provided that when the radiolabel is $^{76}$Br, then the bifunctional linker does not include a phenolic OH group. Non-limiting examples of bifunctional linker groups comprising a heterocyclic imide that can be used to link the affibody fragment and radiolabel include N-[2-benzamidoethyl]maleimide, 4-maleimidobenzophenone (BPMal), succinimidyl 4-(p-maleimidophenyl)butyrate (SMPB), 4-(4-N-maleimidophenyl)butyric acid hydrazide hydrochloride (MPBH), and maleimidobenzoyl-N-hydroxysuccinimide ester (MBS). When the affibody is radiolabeled with $^{76}$Br, then the bifunctional linker does not include a 4-hydroxyphenyl group.

In an embodiment, the bifunctional linker is

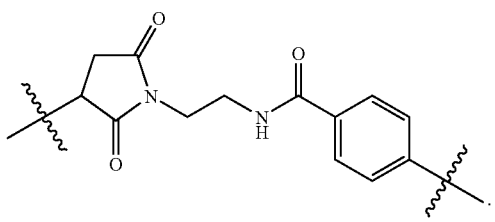

This linker can be prepared from N-[2-benzamidoethyl]maleimide, which is subsequently radiolabeled with $^{18}$F to form N-[2-(4-($^{18}$F-fluorobenzamido)ethyl]maleimide. The compound can be similarly radiolabeled with $^{76}$Br. Syntheses of this compound are described herein and in Cai et al. (*The Journal of Nuclear Medicine*, 47(7): 1172-1180 (July 2006)).

In another embodiment, the bifunctional linker is

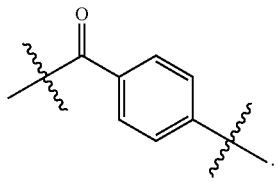

This linker can be prepared from 2,5-dioxocyclopentyl benzoate, which is subsequently radiolabeled with either $^{18}$F or $^{76}$Br.

Any suitable $^{18}$F-containing label can be used. Preferably, the radiolabel is $^{18}$F. $^{18}$F has a half-life ($t_{1/2}$) of 110 minutes, emits β+ particles at an energy of 635 keV, and is 97% abundant. $^{18}$F can be obtained from cyclotrons after bombardment of $^{18}$O-enriched water with protons. The enriched water containing H-$^{18}$F can be neutralized with a base having a counter-ion that is any alkali metal (M), such as potassium or another monovalent ion, and the water can be evaporated off to give a residue of M-$^{18}$F, which can be taken up in an organic solvent for further use. In general, the counter-ion is selected to enable the fluoride ion to react rapidly in an organic phase with a halogen. Potassium is generally used as a counter-ion because it is cheaper than cesium. However, with carrier-free $^{18}$F, trivial amounts of counter-ion are required, and the counter-ion cost is minimal.

Cesium is useful as a counter-ion since it is a larger ion with a more diffuse charge. Accordingly, cesium has looser ionic interactions with the small fluoride atom, and therefore does not interfere with the nucleophilic properties of the fluoride ion. For similar reasons, potassium is preferred to sodium, and, in general, the suitability of a Group Ia metal as a counter-ion in accordance with the present invention increases down the periodic table. Group Ib reagents, such as silver, also are useful as counter-ions. Further, organic phase transfer-type ions, such as tetraalkylammonium salts, also can be used as counter-ions.

Fluoride can have a tendency to become hydrated and lose its nucleophilic character. To minimize this, the labeling reaction is preferably performed under anhydrous conditions. For example, fluoride (as potassium fluoride or as a complex with any of the other counter-ions discussed above) can be placed in organic solvents, such as acetonitrile or tetrahydrofuran. With the help of agents which bind to the counter-ion, such as Kryptofix 2.2.2 (4,7,13,16,21,24-hexaoxa-1,10-diazabicyclo[8.8.8]-hexacosane), the fluoride ion is very nucleophilic in these solvents.

Any suitable $^{76}$Br-containing label can be used. Preferably, the radiolabel is $^{76}$Br. $^{76}$Br has a half-life ($t_{1/2}$) of 16 h, emits β+ particles at an energy of 3.98 MeV, emits gamma particles, and is 9.1% abundant. $^{76}$Br can be purchased commercially, produced in a cyclotron at a PET center, or prepared by a synthesis known in the art (e.g., Mume et al., *Bioconjugate Chem.*, 16: 1547-1555 (2005)).

In an embodiment of the invention, the radiolabeled affibody molecule is

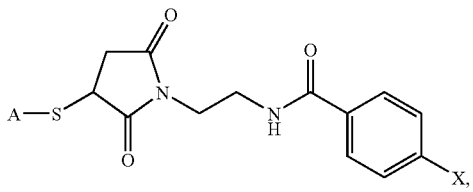

wherein X is $^{18}$F or $^{76}$Br and A-S is the His$_6$-Z$_{HER2:342}$ fragment of an IgG-binding domain of protein A from *Staphylococcus aureus*.

The invention further provides a pharmaceutical composition comprising a pharmaceutically acceptable carrier and a radiolabeled affibody molecule. Pharmaceutically acceptable carriers, for example, vehicles, adjuvants, excipients, and diluents, are well-known to those ordinarily skilled in the art and are readily available to the public. The choice of carrier will be determined, in part, by the particular composition and by the particular method used to administer the composition. Accordingly, there are a wide variety of suitable formulations of the pharmaceutical compositions of the present invention.

One skilled in the art will appreciate that suitable methods of administering a composition of the present invention to an animal, e.g., a mammal such as a human, are also known. Although more than one route can be used to administer a particular composition, a particular route can provide a more immediate and more effective result than another route.

Formulations suitable for oral administration can consist of (a) liquid solutions, such as an effective amount of the radiolabeled affibody molecule dissolved in a diluent, such as water or saline, (b) capsules, sachets or tablets, each containing a predetermined amount of the active ingredient, as solids or granules, (c) suspensions in an appropriate liquid, and (d) suitable emulsions.

Tablet forms can include one or more of lactose, mannitol, cornstarch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The radiolabeled affibody molecule, alone or in combination with other suitable components, can be made into aerosol formulations to be administered via inhalation. These aerosol formulations can be placed into pressurized acceptable propellants, such as dichlorodifluoromethane, hydrofluorocarbon (such as HFC 134a and/or 227), propane, nitrogen, and the like.

Formulations suitable for parenteral administration include aqueous and non-aqueous solutions, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to a subject, particularly a human, in the context of the present invention should be sufficient to allow for diagnostic imaging of the desired tissue or organ. The dose will be determined by the strength of the particular compositions employed and the condition of the subject (e.g., human), as well as the body weight of the subject (e.g., human) to be diagnosed. The size of the dose also will be determined by the existence, nature, and extent of any adverse side effects that might accompany the administration of a particular composition. A suitable dosage for internal administration is 0.01 to 100 mg/kg of body weight per day, such as 0.01 to 35 mg/kg of body weight per day or 0.05 to 5 mg/kg of body weight per day. The dosage of the active ingredient, the radiolabeled affibody molecule will comprise generally a low concentration of the overall composition (e.g., 1-1000 µCi/kg of body weight, 10-500 µCi/kg of body weight, or 50-250 µCi/kg of body weight). The term "Ci" refers to a Curie, which is the basic unit to describe the intensity of a radioactivity in a sample of material.

The human epidermal growth factor receptor HER2 (Her2/neu, ErbB2, or c-erb-b2) is a growth factor receptor that is expressed on many cell types. HER2-proteins are over-expressed in a number of cancer types, such as breast cancer, ovarian cancer, salivary gland cancer, stomach cancer, kidney cancer, colon cancer, prostate cancer, and non-small cell lung cancer. See, for example, Mass (*Int. J. Radial. Oncol. Biol. Phys.*, 58(3): 932-940 (2004)), Wang et al. (*Semin. Oncol.*, 28(5 Suppl. 16): 115-124 (2001)), and Scholl et al. (*Ann. Oncol.*, 12(Suppl. 1): S81-S87 (2001)). When over-expressed, homo- or heterodimers of HER2 cause increased proliferation, decreased apoptosis, enhanced tumor cell motility and neo-angiogenesis, which are all traits strongly associated with tumor formation. Research has shown that women with HER2-positive breast cancer have a more aggressive disease, greater likelihood of recurrence, poorer prognosis, and decreased survival compared to women with HER2-negative breast cancer.

The epidermal growth factor receptor (EGFR, ErbB) is a cell surface glycoprotein of approximately 135 kD (unglycosylated). The EGFR is over-expressed or mutated in many types of cancers, including breast cancer, glioblastoma multiforme, lung cancer, head and neck cancer, ovarian cancer, cervical cancer, bladder cancer, and esophageal cancer. See, for example, Nicholson et al. (*Eur. J. Cancer*, 37(Suppl 4): S9-15 (2001)). The EGFR belongs to the family tyrosine kinase receptors which are characterized by an extracellular binding domain, a single transmembrane, and an intracellular domain responsible for transducing the signal. The receptor dimerizes upon binding to EGFR and the transduced signal stimulates cell growth and differentiation.

Thus, the present invention further provides a method of locating a receptor, such as HER2 or EGFR that is overexpressed in a tissue or organ of a subject. The method comprises the steps of:

a) administering a radiolabeled affibody molecule described herein to the subject, b) obtaining a diagnostic image of the tissue or organ, c) determining the location of radiolabeled affibody molecule bound to the tissue or organ, and d) correlating the location of the bound radiolabeled affibody molecule with the location of the receptor (e.g., HER2 or EGFR) in the subject.

Preferably, the radiolabeled affibody molecule is administered in an amount effective to provide an image.

The term "subject" used herein includes humans, sheep, horses, cattle, pigs, dogs, cats, rats, and mice.

The tissue or organ in the subject to be tested is any tissue or organ that is known to overexpress a receptor such as HER2 or EGFR. Such tissues and organs include the entire organ or a tissue sample of a breast, an ovary, a salivary gland, a stomach, a kidney, a colon, a lung, a cervix, a bladder, a head, or a neck, including an esophagus. The tissue can also include a human cancer cell line known to overexpress HER2, EGFR, or both. Such cell lines include SKBR-3 (breast cancer), BT-474 (breast cancer), MDA-MB-453 and -468 (both breast cancer), MCF7 (breast cancer), SKOV-3 (ovarian cancer), H2122 (non-small cell lung cancer), H661 (non-small cell lung cancer), Calu3 (non-small cell lung cancer), H322 (non-small cell lung cancer), A549 (non-small cell lung cancer), and SNU-1, -5, -620 (all gastric cancer).

Obtaining a diagnostic image of the tissue or organ in step b) typically comprises exposing the tissue or organ in the subject to an energy source, whereupon a diagnostic image of the tissue or organ is obtained. The diagnostic image can be, for example, positron emission tomography (PET) image, a magnetic resonance image (MRI), a computerized tomography (CT) scan, single photon emission computed spectroscopy (SPECT) image, or the like.

The diagnostic image can be an MRI. When administered to a subject, the radiolabeled affibody molecule distributes in various concentrations to different tissues, and catalyzes the relaxation of protons in the tissues that have been excited by the absorption of radiofrequency energy from a magnetic resonance imager. This acceleration of the rate of relaxation of the excited protons provides for an image of different contrast when the subject is scanned with a magnetic resonance imager. The magnetic resonance imager is used to record images at various times, generally either before and after administration of the $^{18}$F labeled affibody molecule, or after administration only, and the differences in the images created by the presence of the radiolabeled affibody molecule in tissues are used in diagnosis. Guidelines for performing imaging techniques can be found in Stark et al., *Magnetic Resonance Imaging*, Mosbey Year Book: St. Louis, 1992, hereby incorporated by reference.

Single Positron Emission Computed Tomography (SPECT) is a non-invasive imaging method to localize the position of a target such as a cancer metastasis, based on radioactive substances that emit gamma radiation when decaying.

A CT scan provides anatomical detail, such as size and location of the tumor or mass. Digital geometry processing is used to generate a three-dimensional image of the internals of an object from a large series of two-dimensional X-ray images taken around a single axis of rotation. CT produces a volume of data which can be manipulated, through a process known as windowing, in order to demonstrate various structures based on their ability to block the X-ray beam. Combined techniques such as PET/CT and PET/MRI are suitable for use in the invention.

Preferably, step b) comprises obtaining a positron emission tomography (PET) image of the tissue or organ. PET is a non-invasive imaging method to localize the position of a target such as a cancer metastasis. In PET, 511 keV gamma photons produced during positron annihilation decay are detected. A positron-emitting radionuclide, such as $^{18}$F or $^{76}$Br, is introduced, usually by injection, and accumulates in the target tissue or organ. As it decays it emits a positron, which promptly combines with a nearby electron resulting in the simultaneous emission of two identifiable gamma rays in opposite directions. These are detected by a PET camera and give very precise indication of their origin. A PET scan can provide in vivo physiology such as metabolic detail (e.g., cellular activity) of the tumor or mass. The diagnosis is at a molecular level thereby providing detection of a tumor or mass at an early stage.

Since PET is a quantitative tool, the present invention provides a method of measuring the quantity of a receptor, such as HER2 or EGFR that is overexpressed in a tissue or organ of a subject. The method comprises the steps of:

a) administering a radiolabeled affibody molecule described herein to the subject, b) obtaining a positron emission tomography (PET) image of the tissue or organ, c) determining the amount of radiolabeled affibody molecule bound to the tissue or organ, d) correlating the amount of the bound radiolabeled affibody molecule with the quantity of receptor (e.g., HER2 or EGFR) in the subject.

In conjunction with the above-described methods, the present invention further provides a method of quantifying HER2 or EGFR expression in a tissue or organ of a subject before and after administration of an agent that decreases HER2 or EGFR expression. It is contemplated that this method is useful as a non-invasive means to determine the effectiveness of an anticancer agent in decreasing HER2 or EGFR expression from a tumor, which can be indicative of tumor shrinkage and/or reduction. The method comprises the steps of:

a) administering a radiolabeled affibody molecule described herein to the subject, b) obtaining a positron emission tomography (PET) image of the tissue or organ, c) determining a first amount of radiolabeled affibody molecule bound to the tissue or organ, d) correlating the first amount of the bound radiolabeled affibody molecule with a first quantity of receptor (e.g., HER2 or EGFR) in the subject, (e) administering an agent that decreases the quantity of receptor (e.g., HER2 or EGFR) to the subject, f) obtaining a second positron emission tomography (PET) image of the tissue or organ, g) determining a second amount of radiolabeled affibody molecule bound to the tissue or organ, and h) correlating the second amount of the bound radiolabeled affibody molecule with a second quantity of receptor (e.g., HER2 or EGFR) in the subject.

Suitable agents that decrease EGFR expression include anticancer agents known in the literature (e.g., gefitinib, erlotinib, matuzumab, geldanamycin, derivatives of geldanamycin). Suitable agents that decrease HER2 expression include anticancer agents known in the literature (e.g., geldanamycin, derivatives of geldanamycin, trastuzumab (Herceptin™), gefitinib). Derivatives of geldanamycin include 17-allylamino-17-demethoxygeldanamycin (17-AAG), 17-dimethylaminoethylamino-17-demethoxygeldanamycin (17-DMAG), and other derivatives described in, for example, U.S. Pat. Nos. 4,261,989, 6,890,917, 6,747,055, and 7,026,350, the contents of which are incorporated by reference.

Preferably, an agent that decreases HER2 expression is an inhibitor of Hsp90. Hsp 90 is a ubiquitous molecular chaperone critical for the folding, assembly and activity of multiple mutated and overexpressed signaling proteins that promote the growth and/or survival of tumor cells. Binding of geldanamycin or a derivative thereof to Hsp 90 causes the destabilization and degradation of its client proteins, such as HER2. Preferred compounds that inhibit Hsp90 include geldanamycin, 17-AAG, 17-DMAG, and other geldanamycin derivatives described in, for example, U.S. Pat. Nos. 4,261,989, 6,890,917, 6,747,055, and 7,026,350, the contents of which are incorporated by reference.

The following examples further illustrate the invention but, of course, should not be construed as in any way limiting its scope.

EXAMPLE 1

This example illustrates a preparation of $^{18}$F-labeled $His_6$-$Z_{Her2:342}$-Cys affibody molecule.

[$^{18}$F]Fluorobenzoic acid is prepared as previously described using a manual synthesis method (Kiesewetter et al., *Nuclear Medicine and Biology*, 30: 11-24 (2003)) Pentamethylbenzyl (4-trimethylammonium) benzoate trifluoromethanesulfonate (3 mg, 6 μmol) is treated with [$^{18}$F]fluoride in the presence of Kryptofix [2.2.2] (6 μmol) and $K_2CO_3$ (3 μmol) in $CH_3CN$ (0.1 mL). See FIG. 1A. The reaction is heated in a sealed V-vial for 10 min. The solution is diluted with ether (200 μL) then transferred to a short column of silica gel. The vial is rinsed with an additional portion of ether and this volume is added to the silica column. The column is eluted with an additional 400 μL of ether. Anisole (10 μL) is added to the collection tube prior to elution. The combined ether eluant is evaporated to near dryness.

The intermediate is treated with trifluoroacetic acid to provide crude 4-[$^{18}$F]fluorobenzoic acid. The trifluoroacetic acid is evaporated at ice temperature, and the residue is treated with aminoethylmaleimide (1.52 mg, 6 μmol), diethyl cyanophosphonate (1.3 mg, 8 μmol), and diisopropylethylamine (10 mL). The resulting solution is heated at 70° C. for five minutes. This reaction is diluted with 150 mL water and injected onto an HPLC (high performance liquid chromatography) column (Luna C-18 (Phenomenex), 10×250 mm, 20% $CH_3CN$, 80% water). The product eluting at about 17 min is collected, diluted to about 20 mL with water, and trapped on a BondElut C-18 column (500 mg). The product is eluted from the column with $CH_2Cl_2$, dried, and carefully evaporated in the bottom of a 1.5 mL eppendorf tube.

Figure 1B:
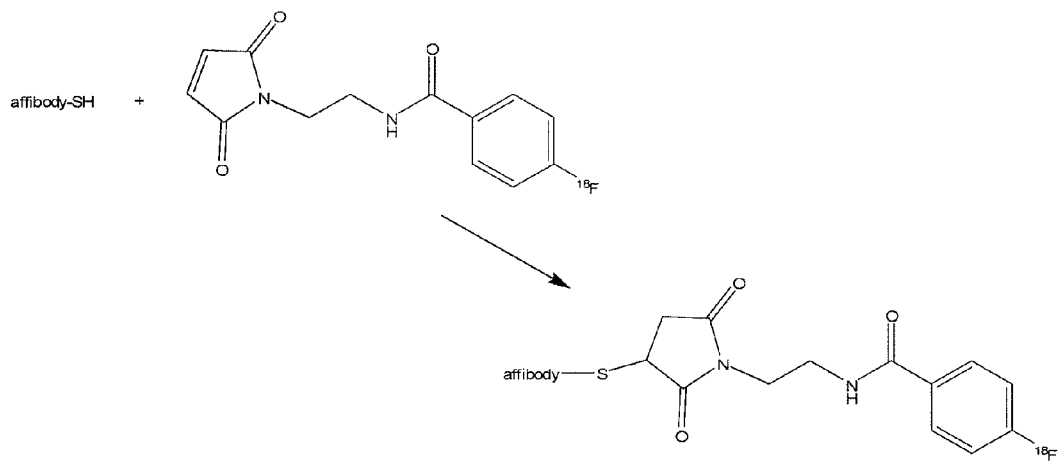
FIG. 1B depicts a preparation of an $^{18}$F radiolabeled affibody molecule, wherein the affibody (e.g., His$_6$-($Z_{HER2:342}$)-Cys) is linked to the $^{18}$F label via a maleimide bifunctional linker.

The N-[2-(4-($^{18}$F-fluorobenzamido)ethyl]maleimide residue is treated with 10 mL of ethanol and a PBS (phosphate buffered saline) solution of affibody ($His_6$-($Z_{HER2:342}$)-Cys) (40 μL containing 100 mg, 12 nmol) that has been treated with TCEP (tris(2-carboxyethyl)phosphine HCl) (2 μg, 7 nmol) for approximately 1 h. See FIG. 1B. This solution is incubated for 15 min and loaded onto a NAP-5 column (Amersham). The NAP-5 column is eluted with 250 μL portions of PBS. The most concentrated fraction containing the radiolabeled protein is collected and used for the biologically experiments. The radiochemical yield of $^{18}$F labeled affibody conjugate using this un-optimized procedure is approximately 5% based on starting [$^{18}$F] fluoride and uncorrected for decay. The procedure takes about two hours to complete.

EXAMPLE 2

This example demonstrates the in vitro binding of the resulting $^{18}$F labeled affibody molecule as characterized by receptor saturation and competitive binding studies using human, HER2-overexpressing breast and ovarian cancer cell lines, SKBR-3 and SKOV-3, respectively.

HER2-overexpressing SKBR-3 human breast cancer cell line (American Type Culture Collection) is cultured in DMEM/F12 (Dulbecco's Modified Eagle's Medium/Ham's F12) medium with 10% fetal bovine serum (FBS) at 37° C.

In vitro binding characteristics of the $^{18}$F radiolabeled affibody molecule (ligand) are assessed using saturation and displacement cell-binding assays. The day before the experiments are begun, the cells are seeded in 6-well plates at a concentration of $5\times10^5$ cells per well. For receptor saturation analysis, the cells are incubated with increasing concentrations of $^{18}$F-affibody molecule alone (total binding). Another set of samples, exposed to 100-fold excess of non-labeled affibody for 30 min before $^{18}$F-affibody molecule is added, is used to assess the nonspecific binding.

Figure 2A:
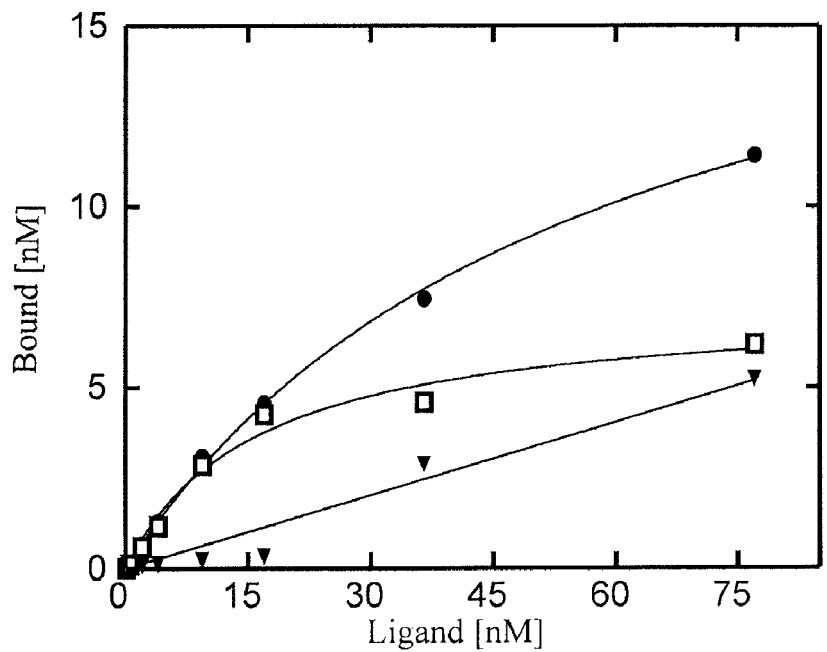
FIG. 2A and 2B depict in vitro binding specificity of $^{18}$F-$Z_{HER2}$-affibody molecules in accordance with an embodiment of the invention.

The cells are washed twice with cold, serum free medium and then 400 μL of radiolabeled affibody and 200 μL of 1×PBS are added. The cells are incubated at 4° C. for 2 h. The incubation medium is collected, the cells are washed two times with cold PBS and incubated with 400 μL of trypsin/EDTA at 37° C. When the cells detach, 400 μL PBS is added to each well, and the cell suspension is transferred to the 20 mL scintillation vials for radioactivity measurements by a γ-counter (1480 Wizard 3, Automatic Gamma Counter, PerkinElmer). The results are summarized in FIG. 2A.

Figure 2B:
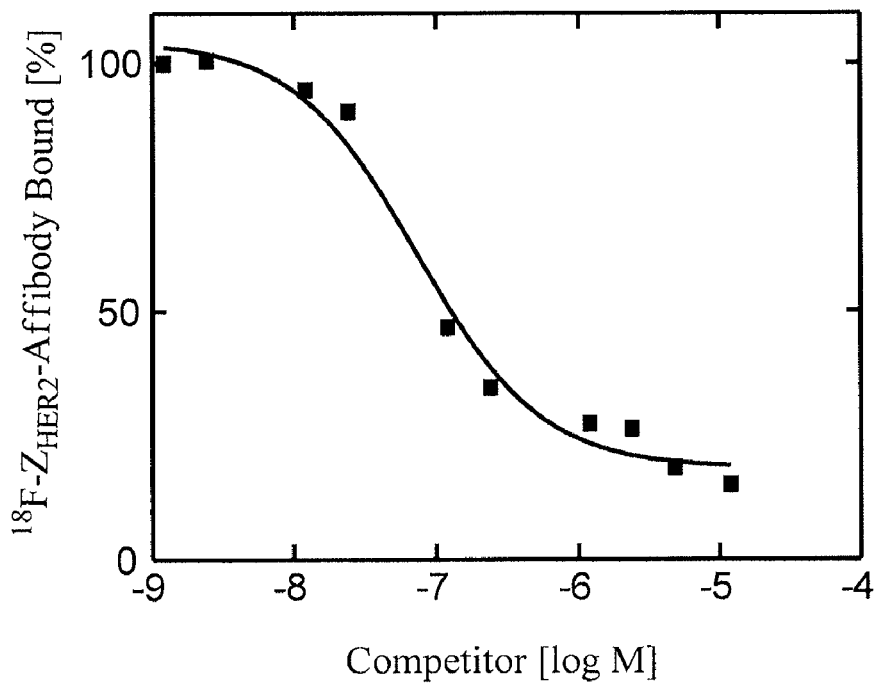

For the displacement assay, the cells are incubated with $^{18}$F-affibody molecules (final concentration approximately 0.9 ng/μL) and increased concentrations (0.01-100 ng/μL) of non-labeled competitor (non-labeled affibody). The remainder of the experimental procedures is the same as those used for saturation studies discussed above. The binding of $^{18}$F-affibody molecules decreased by the presence of non-labeled affibody is expressed as a percentage of maximum $^{18}$F-affibody binding. Each point is run in triplicate. The best-fit $IC_{50}$ (inhibitory concentration of 50%) values for SKBR-3 cell line are calculated by fitting the data by nonlinear regression using GraphPad Prism (GraphPad Software, Inc.). Experiments are performed twice, and the assays are repeated using different batches of cultured cells for each test chemical. The results are summarized in FIG. 2B.

Figure 3:
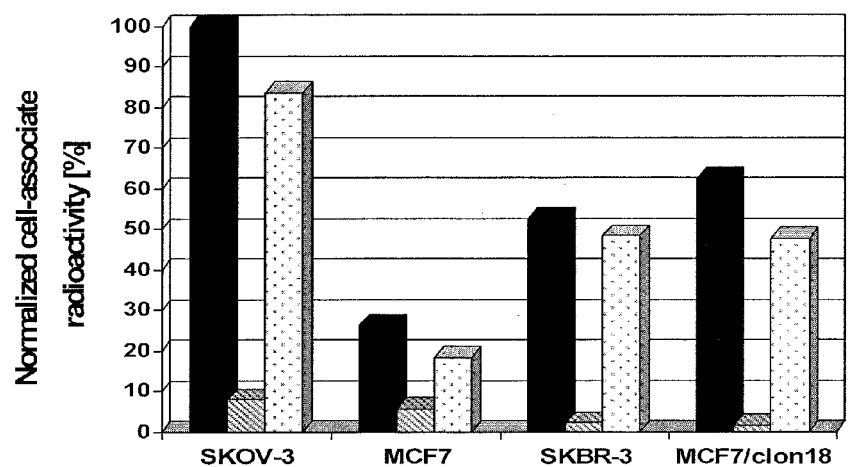
FIG. 3 illustrates the binding of $^{18}$F-$Z_{HER2}$-affibody molecules to cells with different levels of HER2 expression (cell line versus normalized cell-associated radioactivity (%)) and the effect of pre-incubation with either affibody molecules or Herceptin™ on the binding. The black bars represent $^{18}$F-$Z_{HER2}$-affibody binding; the striped bars represent binding after blocking; and the dotted bars represent binding after addition of Herceptin™.

FIG. 3 shows the binding of the $^{18}$F-$Z_{HER2}$-affibody molecules to cells with different levels of HER2 expression. The samples are exposed to the radioconjugate with or without 100-fold excess of either non-labeled affibody molecules or Herceptin™.

EXAMPLE 3

This example illustrates the tumor uptake of $^{18}$F-affibody in SKOV-3 xenograft-bearing nude mice.

The animal experiments are performed under a protocol approved by NIH Animal Care and Use Committee. The SKOV-3 ovarian cancer model is established by subcutaneous injection of $1.5\times10^7$ cells into the right hind leg of female athymic nude mice 8 weeks before the experiment. The mice are injected with 100 μL (98.1 μCi) of $^{18}$F-affibody into the tail vein. For biodistribution studies, mice are sacrificed after 1 h to 4 h following the administration of the radioconjugate and the selected organs are dissected, weighed, and their radioactivity is measured using a γ-counter.

PET scans are performed using the Advanced Technology Laboratory Animal Scanner (ATLAS, Seidel et al., *IEEE Transactions on Nuclear Science*, 50: 1347 (2003)). The scanner has a computer controlled bed and 8 cm in diameter with a useful transverse field-of-view (FOV) of 6 cm and an axial field-of-view of 2 cm. It operates exclusively in the 3-dimensional list mode. Animals are placed near the center of FOV of the ATLAS scanner, where the highest image resolution and sensitivity are available. The 60-min dynamic (1×10 min) data acquisition (total of 6 frames) is started about 2 min after radiotracer injection. Later time-point static images are also acquired as 15-min static images. The images are reconstructed by a 2-dimensional ordered-subsets expectation maximum algorithm and no correction is applied for attenuation or scatter. For each scan, regions of interest are drawn over the tumor, normal tissue, and major organs. The maximum radioactivity concentration (accumulation) within the tumor or organs is obtained from the maximum grey values within the multiple ROIs (region of interest). The results are calculated as a percentage injected dose per gram (% ID/g). See FIGS. 4-7.

Figure 5:
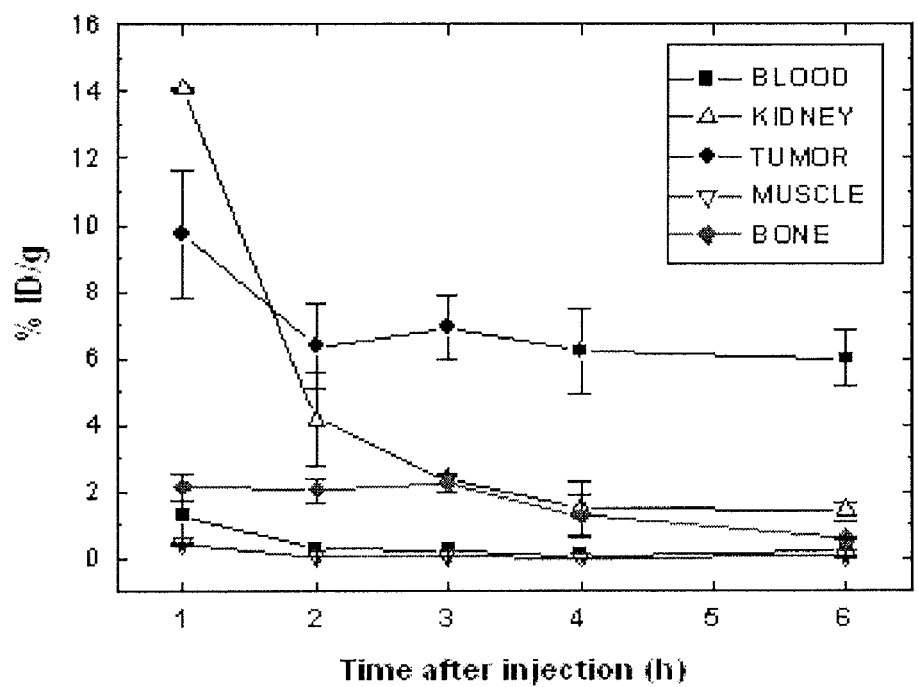
FIG. 5 depicts the time course and ratios of radioactivity accumulation in selected organs shown as time after injection versus % ID/g.

In FIG. 5, the time course and ratios of radioactivity accumulation in selected organs are depicted graphically. The data are also summarized in Table 1.

TABLE 1

Radioactivity Accumulation in Selected Organs

| Ratio | Time (h) | | |
|---|---|---|---|
| | 1 | 2 | 4 |
| Tumor/blood | 7.5 | 23.5 | 69 |
| Tumor/kidney | 0.7 | 1.5 | 4.1 |
| Tumor/muscle | 21 | 127 | 124 |

Figure 6:
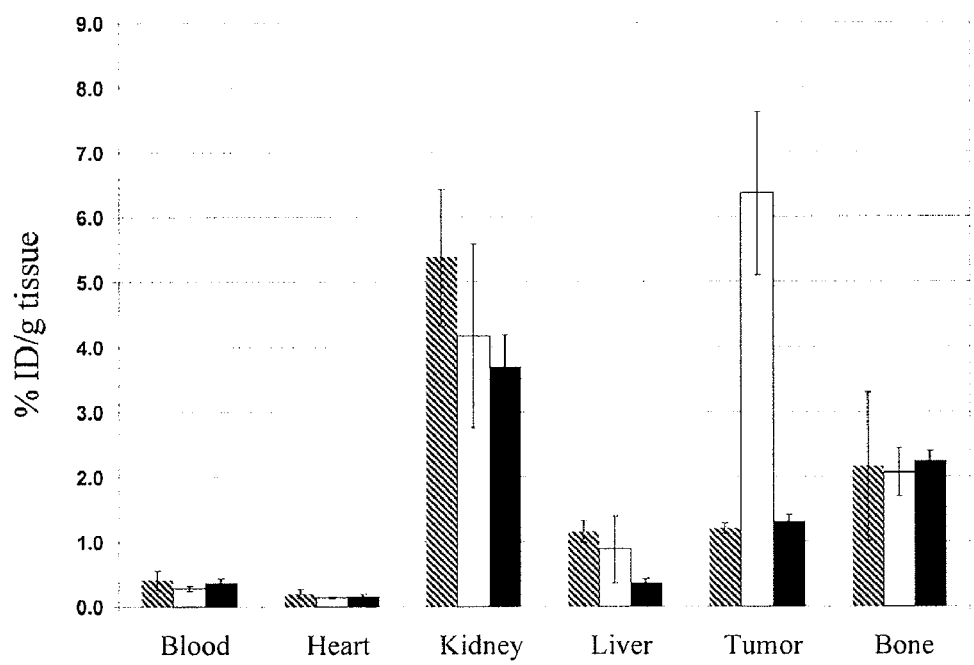
FIG. 6 shows the $^{18}$F-$Z_{HER2}$-affibody uptake in accordance with an embodiment of the invention, 2 h post i.v. injection (~50-60 microCi) in athymic nude mice bearing either HER2-positive SKOV-3 or HER2-negative U251 tumors (tissue type versus % ID/g tissue). The striped bars represent after blocking; the white bars present without blocking; and the black bars represent a negative control.
Figure 7:
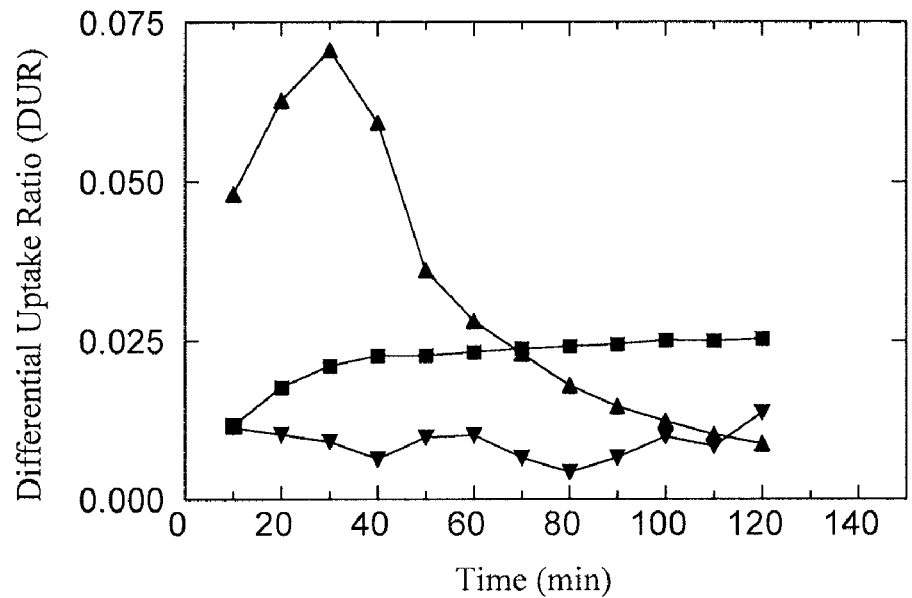
FIG. 7 illustrates quantitative analysis of the PET studies employing an $^{18}$F labeled affibody molecule in accordance with an embodiment of the invention (time versus differential uptake ratio). The symbol ■ represents accumulation in the tumor. The symbol ▲ represents accumulation in the kidney. The symbol ▼ represents accumulation in the bowel.

In FIG. 6, the uptake of the radiolabeled affibody molecule in athymic nude mice bearing either HER2 positive SKOV-3 or HER2 negative U251 tumors measured 2 h post i.v. injection (~50-60 microCi) is shown. As a negative control, one group of animals is pre-injected with 100-fold excess of unlabeled $Z_{HER2}$-affibody to saturate HER2 receptors 45 min before the radiolabeled conjugate is injected.

EXAMPLE 4

This example illustrates that a PET imaging signal from $^{18}$F-$Z_{HER2-342}$-affibody molecules is related to HER2 expression.

To assess the correlation of the signal observed by PET with receptor expression, $^{18}$F-$Z_{HER2-342}$-affibody is administered to athymic nude mice bearing subcutaneous tumors with three different levels of HER2 expression, as determined by Enzyme-Linked ImmunoSorbent Assay (ELISA) assay:

BT-474 (1859 fmol HER2/mg protein (mean));

MCF7/clone18 (1506 fmol HER2/mg protein (mean)), and

MCF7 (28.5 fmol HER2/mg protein (mean)).

Figure 8:
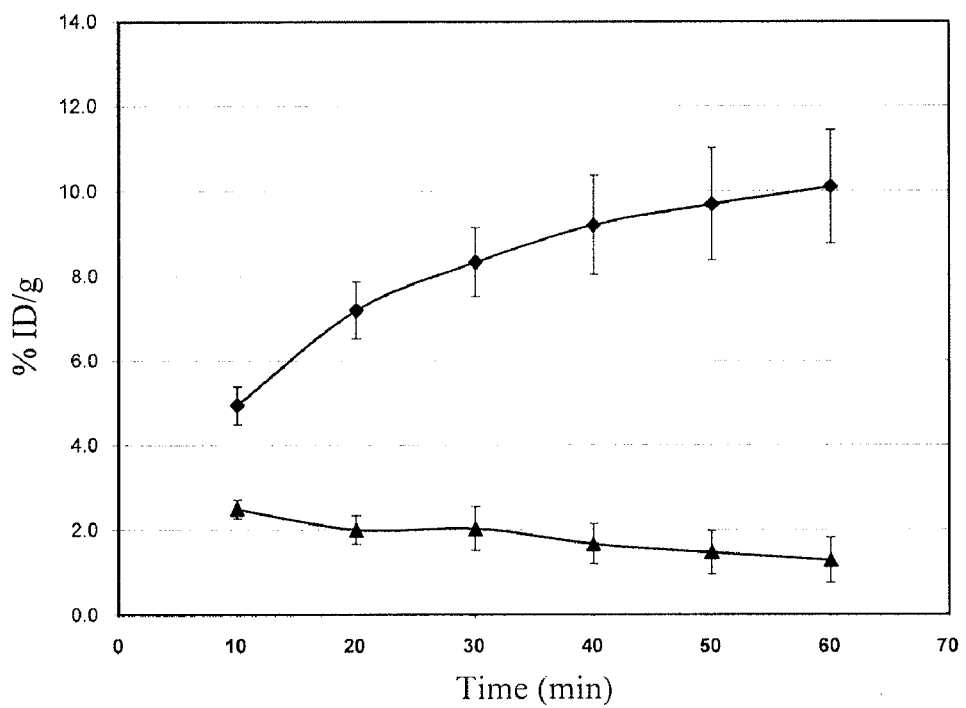
FIG. 8 illustrates quantitative analysis of the PET studies of $^{18}$F labeled affibody molecule uptake in BT-474 tumors in the first hour in accordance with an embodiment of the invention (time versus % ID/g). Acquisition time is 10 minutes per frame for 6 frames. The symbol ♦ represents uptake in the BT-474 tumor, whereas the symbol ▲ represents uptake in the muscle.
Figure 9:
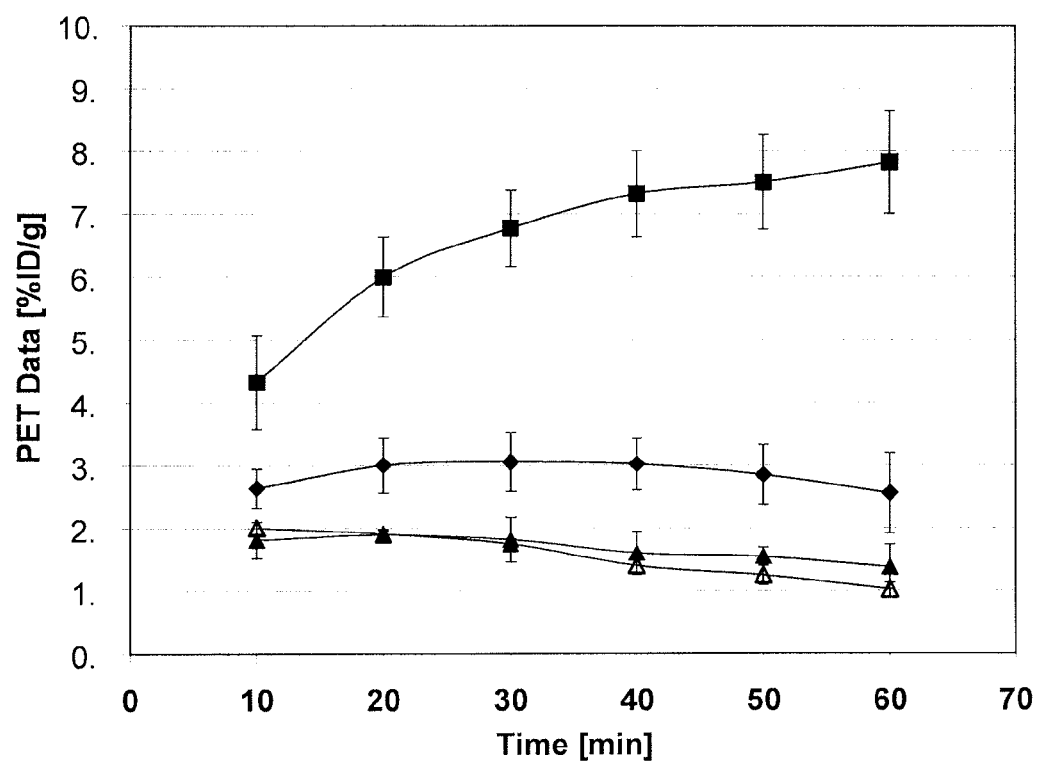
FIG. 9 illustrates quantitative analysis of the PET studies of $^{18}$F labeled affibody molecule uptake in MCF7 and MCF7/clone 18 tumors in the first hour in accordance with an embodiment of the invention (time versus % ID/g). Acquisition time is 10 minutes per frame for 6 frames. The symbol ♦ represents uptake in the MCF7 tumor, whereas the symbol ▲ represents uptake in the MCF7 muscle. The symbol ■ represents uptake in the MCF7/clone 18 tumor, whereas the symbol Δ represents uptake in the MCF7/clone 18 muscle.
Figure 10:
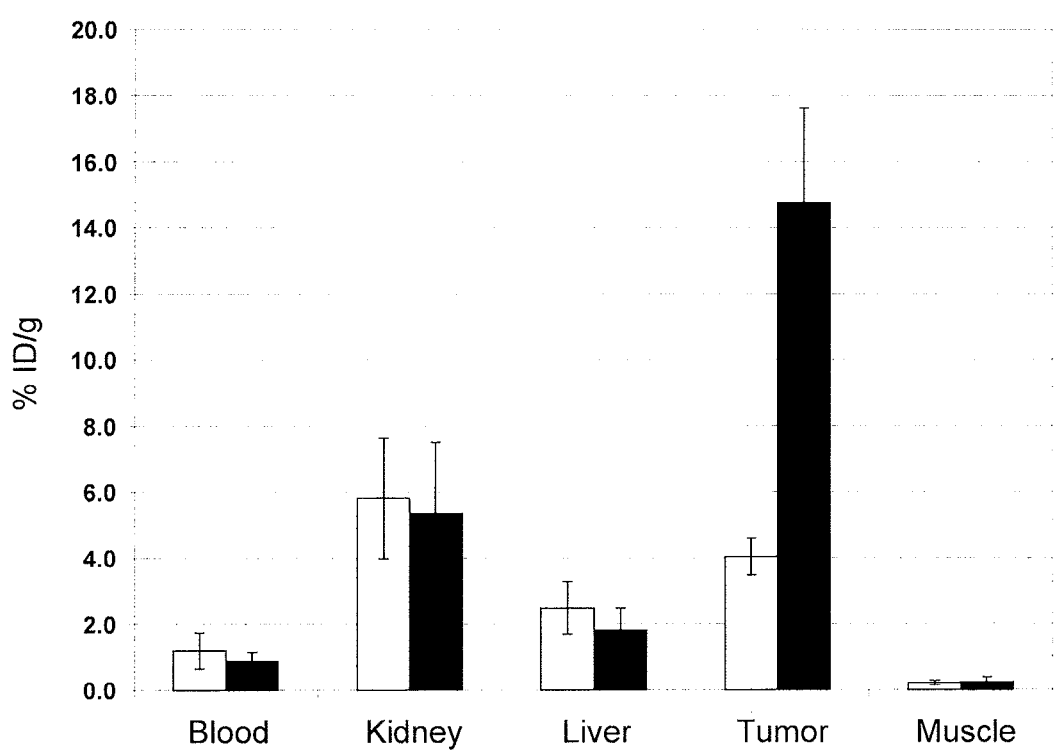
FIG. 10 shows the $^{18}$F-$Z_{HER2}$-affibody uptake in accordance with an embodiment of the invention 2 h post i.v. injection in mice bearing either MCF7 (□) or MCF7/clone 18 (■) tumors (tissue type versus % ID/g tissue).

High contrast PET images between normal and tumor tissue are recorded for BT-474 and MCF7/clone18 tumors. Although low, detectable uptake of the $^{18}$F-$Z_{HER2-342}$-affibody molecule is observed for MCF7 tumors. All of the PET signals correlate well with the number of receptors expressed in each particular cell line. The PET results illustrate that $^{18}$F-$Z_{HER2-342}$-affibody is eliminated quickly from the blood and normal tissues, which provides high tumor/blood and tumor/muscle ratios as soon as 1 h post injection (FIGS. 8 and 9). Two hours post injection, PET ROI analysis indicates a tumor/muscle ratio as high as 22, which is sufficient to obtain high contrast images even at earlier time points. Biodistribution data for all three tumor types show that tumor uptake is higher than uptake in any other organ at 2 h post injection (see, e.g., FIG. 10).

EXAMPLE 5

This example illustrates the quantification of HER2 degradation following administration with 17-DMAG.

Mice bearing BT-474 or MCF7/clone18 subcutaneous tumors are treated with two doses (30-50 mg/kg, 12 or 24 h apart) of 17-DMAG. Animals (n=4-6) are scanned before, 36 h, and 84 h after the treatment. Immediately after the last scan, the animals are euthanized, and the tumors are frozen for further analysis. HER2 expression in the tumors is then measured ex-vivo by western blot (Table 2) and ELISA (Table 3).

TABLE 2

Western Blot Analysis of Tissue Lysates

| | Mean intensity of the signal as expressed as densitometry units (DU) | | |
|---|---|---|---|
| Dry transfer | (1) 120.76 | (2) 86.80 | (3) 43.24 (0.36) |
| | (4) 227.43 | (5) 99.85 (0.44) | (6) 88.68 (0.38) |
| Wet transfer | 243.89 | 193.01 | 83.08 (0.34) |
| | 294.35 | 187.69 (0.63) | 156.39 (0.53) |

TABLE 3

ELISA Analysis of Tissue Lysates.

| | HER2 fmol/mg protein | |
|---|---|---|
| Tissue lysates | Trial 1 | Trial 2 |
| BT-474 control (untreated) | | |
| Animal 1 | 1579.63 | 1840.65 |
| Animal 2 | 1462.05 | 1433.17 |
| | mean: 1520.84 | mean: 1636.82 |
| BT-474 after 17-DMAG | 541.41 (0.35) | 504.86 (0.30) |
| MCF7/clone 18 control (untreated) | 1368.84 | 1434.34 |
| MCF7/clone 18 after 17-DMAG | 602.19 (0.43) | 516.77 (0.36) |

Ex vivo analysis of the tumor samples by western blots and ELISA indicate that the 17-DMAG treatment results in 50-70% decrease of HER2 expression.

Figure 11:
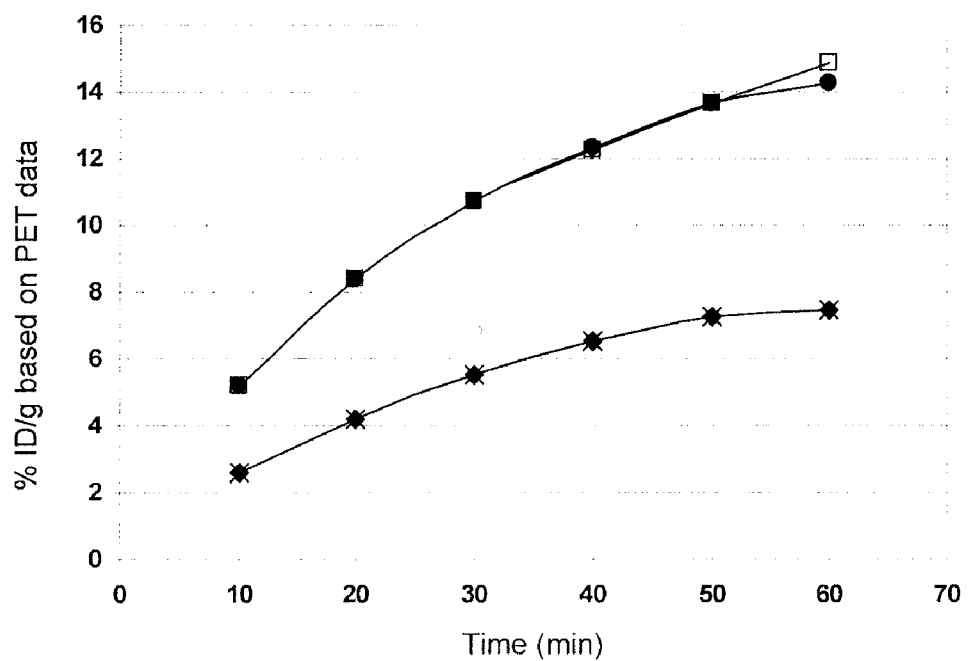
FIG. 11 illustrates a time activity curve of BT-474 tumor uptake before and after administration of 17-DMAG in accordance with an embodiment of the invention (time versus % ID/g). The symbol ● represents uptake before 17-DMAG administration (axial), whereas the symbol ♦ represents uptake after 17-DMAG administration (axial). The symbol ☐ represents uptake before 17-DMAG administration (coronal), whereas the symbol × represents uptake after 17-DMAG administration (coronal).
Figure 12:
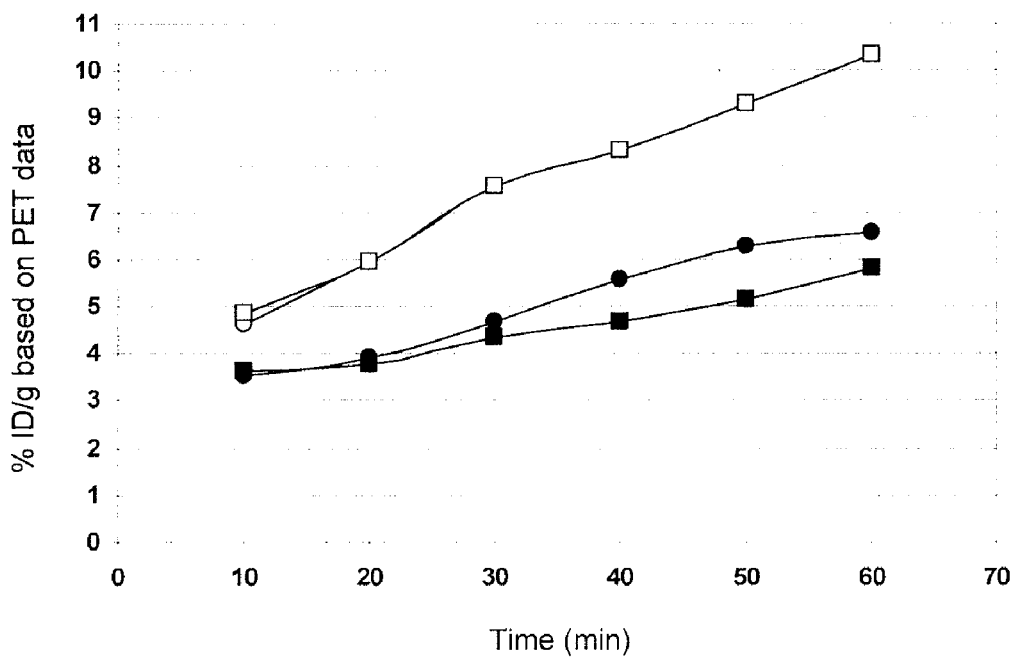
FIG. 12 illustrates a time activity curve of MCF7/clone 18 tumor uptake before and after administration of 17-DMAG in accordance with an embodiment of the invention (time versus % ID/g). The symbol ○ represents uptake before 17-DMAG administration (axial), whereas the symbol ● represents uptake after 17-DMAG administration (axial). The symbol ☐ represents uptake before 17-DMAG administration (coronal), whereas the symbol ■ represents uptake after 17-DMAG administration (coronal).
Figure 13:
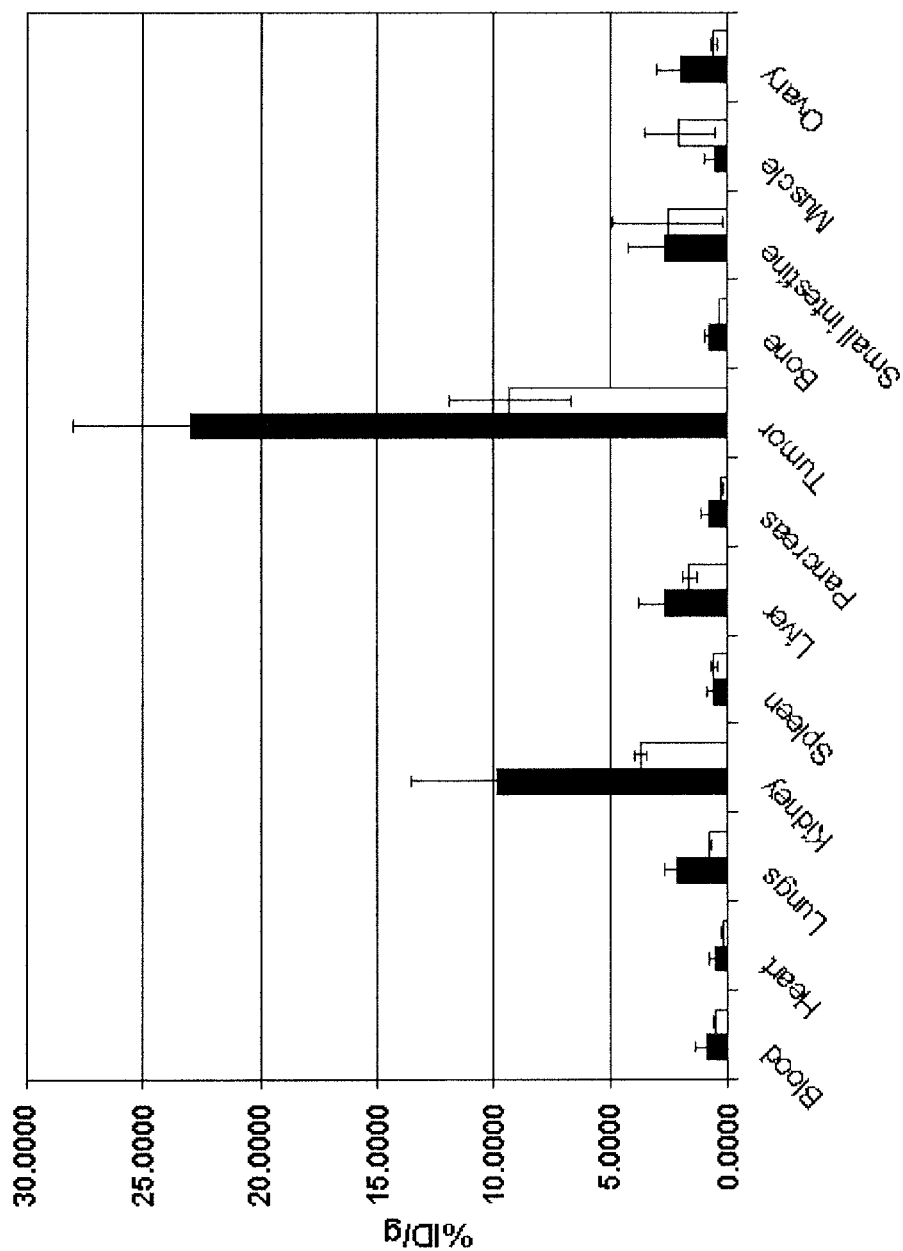
FIG. 13 shows the $^{18}$F-$Z_{HER2}$-affibody uptake in accordance with an embodiment of the invention, 2 h post i.v. injection (black bar) and 2 h post treatment with 17-DMAG (white bar) in mice bearing BT-474 tumors (tissue type versus % ID/g tissue).

In animals treated with 17-DMAG, the accumulation of radioactivity estimated by PET imaging decreases 50-70% at 84 h post-treatment (FIGS. 11 and 12). This change is confirmed by the biodistribution studies, see, e.g., FIG. 13. These results suggest that a $^{18}$F-$Z_{HER2}$-affibody radioconjugate can be used to assess HER2 expression in vivo by PET imaging, thereby providing means to monitor possible changes of receptor expression in response to therapeutic interventions.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A radiolabeled affibody molecule which is

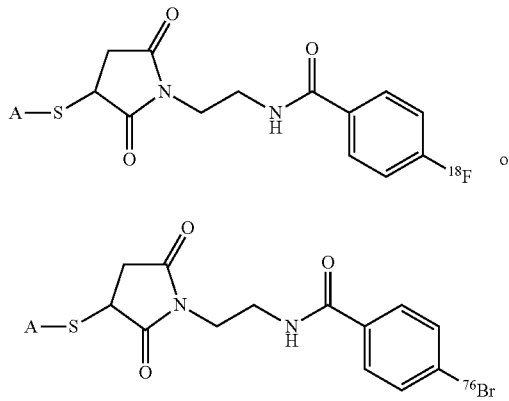

wherein A-S is the $His_6$-$Z_{HER2:342}$-Cys fragment of an IgG-binding domain of protein A from *Staphylococcus aureus*.

2. A pharmaceutical composition comprising the radiolabeled affibody molecule of claim 1 and a pharmaceutically acceptable carrier.

3. A method of locating a receptor that is overexpressed in a tissue or organ of a subject comprising
   a) administering to the subject a radiolabeled affibody molecule which is

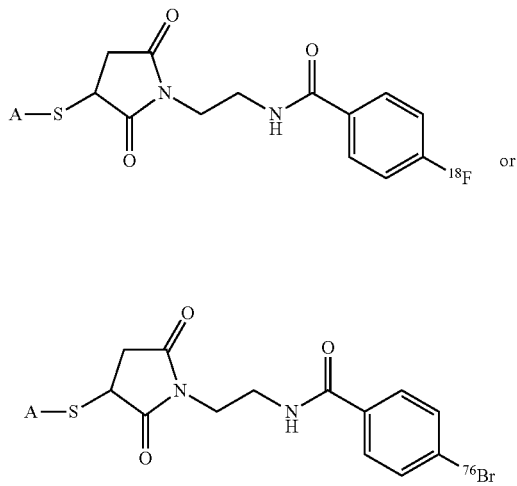

wherein A-S is the $His_6$-$Z_{HER2:342}$-Cys fragment of an IgG-binding domain of protein A from *Staphylococcus aureus*;
   b) obtaining a diagnostic image of the tissue or organ,
   c) determining the location of radiolabeled affibody molecule bound to the tissue or organ, and
   d) correlating the location of the bound radiolabeled affibody molecule with the location of the receptor in the subject.

4. A method of measuring the quantity of a receptor that is overexpressed in a tissue or organ of a subject comprising
   a) administering to the subject a radiolabeled affibody molecule which is

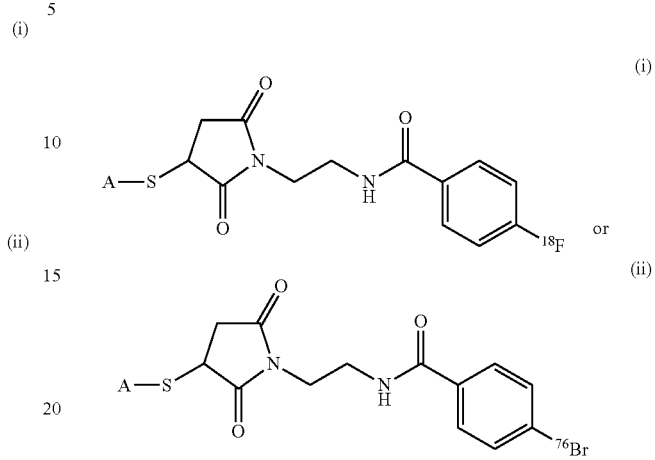

wherein A-S is the $His_6$-$Z_{HER2:342}$-Cys fragment of an IgG-binding domain of protein A from *Staphylococcus aureus*;
   b) obtaining a positron emission tomography (PET) image of the tissue or organ,
   c) determining the amount of radiolabeled affibody molecule bound to the tissue or organ, and
   d) correlating the amount of the bound radiolabeled affibody molecule with the quantity of receptor in the subject.

5. A method of measuring the quantity of a receptor that is overexpressed in a tissue or organ of a subject before and after administration of an agent that decreases expression of the receptor comprising
   a) administering to the subject a radiolabeled affibody molecule which is

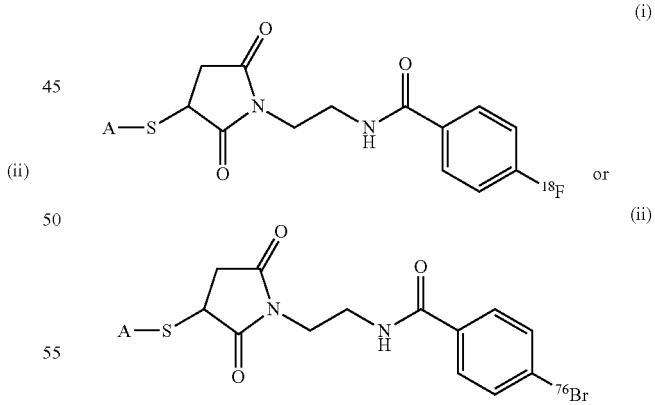

wherein A-S is the $His_6$-$Z_{HER2:342}$-Cys fragment of an IgG-binding domain of protein A from *Staphylococcus aureus*;
   b) obtaining a PET image of the tissue or organ,
   c) determining a first amount of radiolabeled affibody molecule bound to the tissue or organ,
   d) correlating the first amount of the bound radiolabeled affibody molecule with a first quantity of receptor in the subject, e) administering an agent that decreases the quantity of receptor to the subject, f) obtaining a second PET image of the tissue or organ, g) determining a second amount of radiolabeled affibody molecule bound to the tissue or organ, and h) correlating the second amount of the bound radiolabeled affibody molecule with a second quantity of receptor in the subject.

6. The method of claim 3, wherein the diagnostic image is a PET image, a magnetic resonance image (MRI), a computerized tomography (CT) scan, an x-ray contrast image, single photon emission computed spectroscopy (SPECT) image, or a combination thereof.

7. The method of claim 3, wherein step b) comprises obtaining a PET image or SPECT image of the tissue or organ.

8. The radiolabeled affibody molecule of claim 1 which is

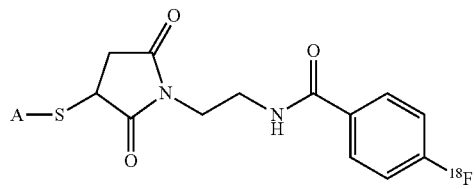

wherein A-S is the His$_6$-Z$_{HER2:342}$-Cys fragment of an IgG-binding domain of protein A from *Staphylococcus aureus*.

9. The radiolabeled affibody molecule of claim 1 which is

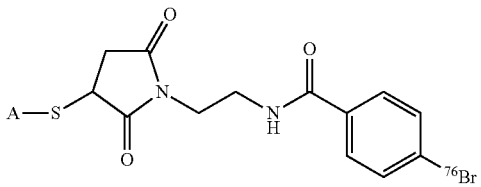

wherein A-S is the His$_6$-Z$_{HER2:342}$-Cys fragment of an IgG-binding domain of protein A from *Staphylococcus aureus*.

10. The method of claim 3, wherein the radiolabeled affibody molecule is

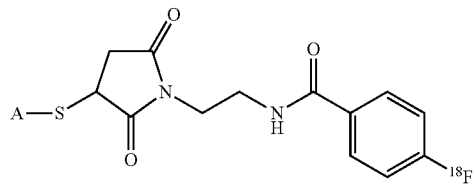

wherein A-S is the His$_6$-Z$_{HER2:342}$-Cys fragment of an IgG-binding domain of protein A from *Staphylococcus aureus*.

11. The method of claim 3, wherein the radiolabeled affibody molecule is

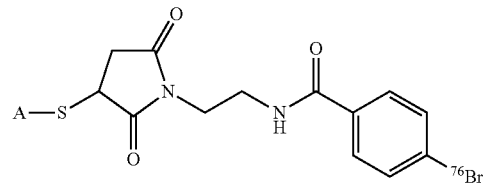

wherein A-S is the His$_6$-Z$_{HER2:342}$-Cys fragment of an IgG-binding domain of protein A from *Staphylococcus aureus*.

12. The method of claim 4, wherein the radiolabeled affibody molecule is

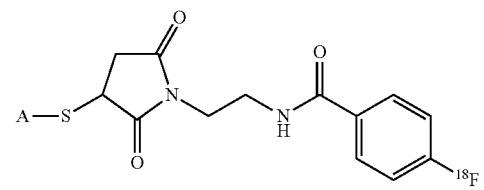

wherein A-S is the HiS$_6$-Z$_{HER2:342}$-Cys fragment of an IgG-binding domain of protein A from *Staphylococcus aureus*.

13. The method of claim 4, wherein the radiolabeled affibody molecule is

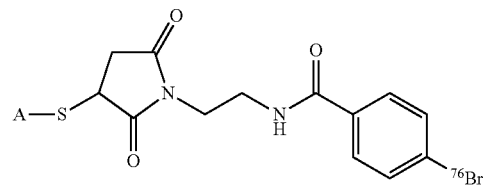

wherein A-S is the HiS$_6$-Z$_{HER2:342}$-Cys fragment of an IgG-binding domain of protein A from *Staphylococcus aureus*.

14. The method of claim 5, wherein the radiolabeled affibody molecule is

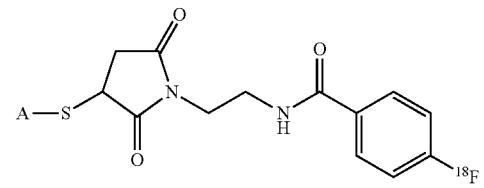

wherein A-S is the His$_6$-Z$_{HER2:342}$-Cys fragment of an IgG-binding domain of protein A from *Staphylococcus aureus*.

15. The method of claim 5, wherein the radiolabeled affibody molecule is

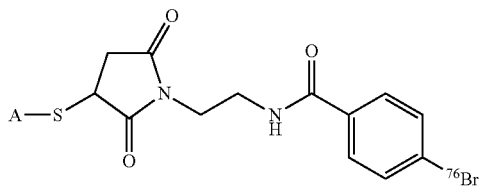

wherein A-S is the $His_6$-$Z_{HER2:342}$-Cys fragment of an IgG-binding domain of protein A from *Staphylococcus aureus*.

16. The pharmaceutical composition of claim 2, wherein the radiolabeled affibody molecule is

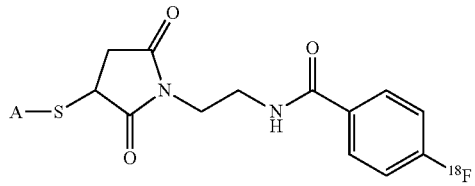

wherein A-S is the $His_6$-$Z_{HER2:342}$-Cys fragment of an IgG-binding domain of protein A from *Staphylococcus aureus*.

17. The pharmaceutical composition of claim 2, wherein the radiolabeled affibody molecule is

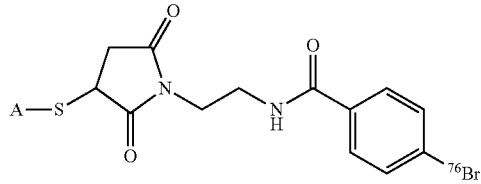

wherein A-S is the $HiS_6$-$Z_{HER2:342}$-Cys fragment of an IgG-binding domain of protein A from *Staphylococcus aureus*.

* * * * *